(12) United States Patent
Ferree

(10) Patent No.: US 8,075,619 B2
(45) Date of Patent: Dec. 13, 2011

(54) DEVICES FOR DISC HERNIATION REPAIR AND METHODS OF USE

(75) Inventor: Bret A. Ferree, Cincinnati, OH (US)

(73) Assignee: Anova Corporation, Summit, NJ (US)

( * ) Notice: Subject to any disclaimer, the term of this patent is extended or adjusted under 35 U.S.C. 154(b) by 1014 days.

(21) Appl. No.: 11/811,751

(22) Filed: Jun. 12, 2007

(65) Prior Publication Data

US 2007/0288040 A1    Dec. 13, 2007

Related U.S. Application Data

(60) Provisional application No. 60/813,232, filed on Jun. 13, 2006, provisional application No. 60/847,649, filed on Sep. 26, 2006.

(51) Int. Cl.
*A61F 2/44* (2006.01)
(52) U.S. Cl. ..................... 623/17.11; 606/279
(58) Field of Classification Search ..... 623/17.11–17.16
See application file for complete search history.

(56) References Cited

U.S. PATENT DOCUMENTS

| 6,224,630 | B1  | 5/2001 | Bao |
| 6,425,919 | B1* | 7/2002 | Lambrecht ................. 623/17.16 |
| 6,733,531 | B1  | 5/2004 | Trieu |
| 2003/0114930 | A1* | 6/2003 | Lim et al. .................. 623/17.11 |

* cited by examiner

*Primary Examiner* — Eduardo C Robert
*Assistant Examiner* — Julianna N. Harvey
(74) *Attorney, Agent, or Firm* — Gifford, Krass, Sprinkle, Anderson & Citkowski, P.C.

(57) ABSTRACT

Devices and methods for fixing defects in the anulus fibrosus (vertebral disc) of a patient are described. The devices a mesh patch; first, second, third, and fourth sutures; and first, second, third, and fourth anchors. Each anchor has a first portion adapted for insertion into a bone and a second portion having an opening. The sutures are disposed through the openings of the anchors. The first portions of the first and second anchors are inserted into a cranial vertebra. The first portions of the third and fourth anchors are inserted into a caudal vertebra. The mesh patch is positioned adjacent the defect. An end of first suture can be attached to an end of the third suture. An end of the second suture can be attached to an end of the fourth suture. The other ends of each of the first, second, third, and fourth sutures can then be anchored.

4 Claims, 33 Drawing Sheets

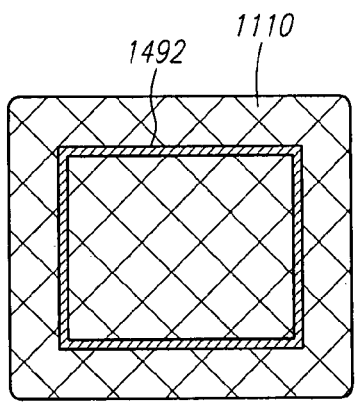
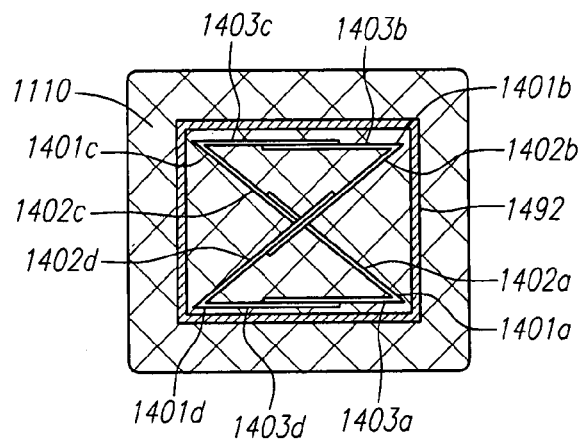
FIG. 16A    FIG. 16B
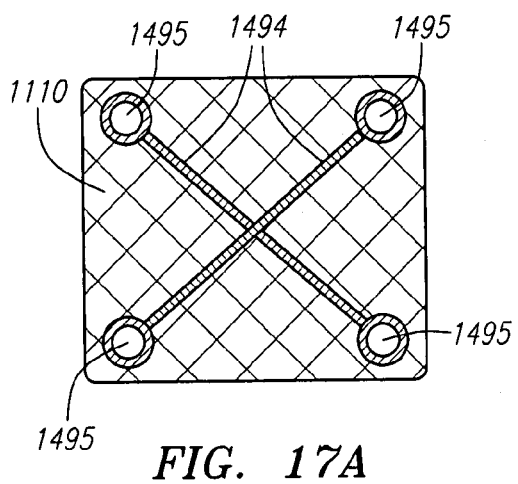
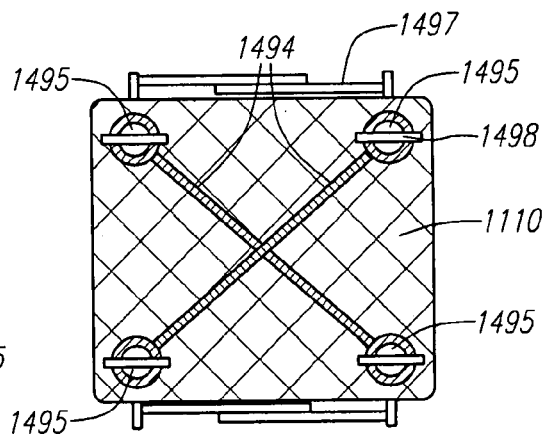
FIG. 17A    FIG. 17B
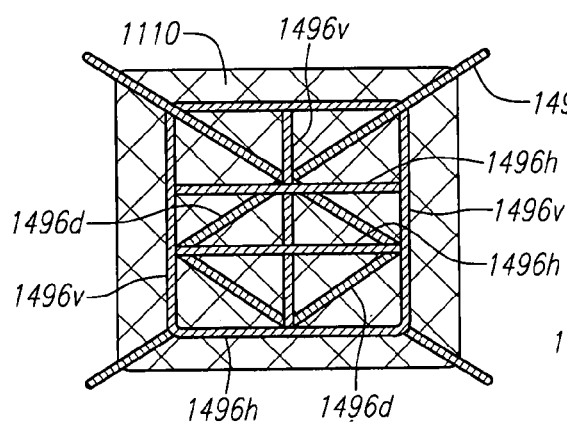
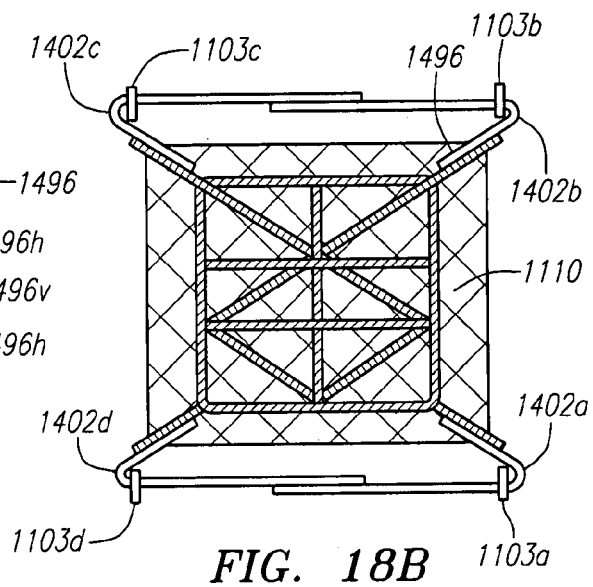
FIG. 18A    FIG. 18B

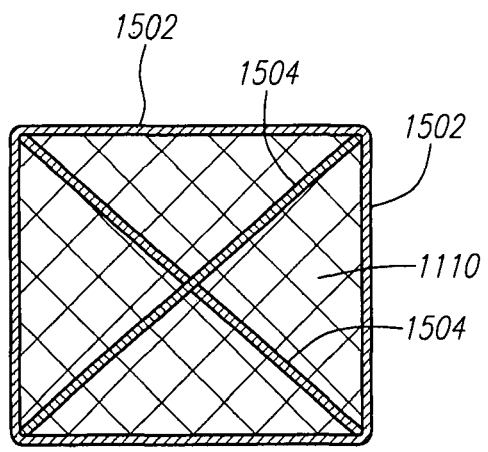 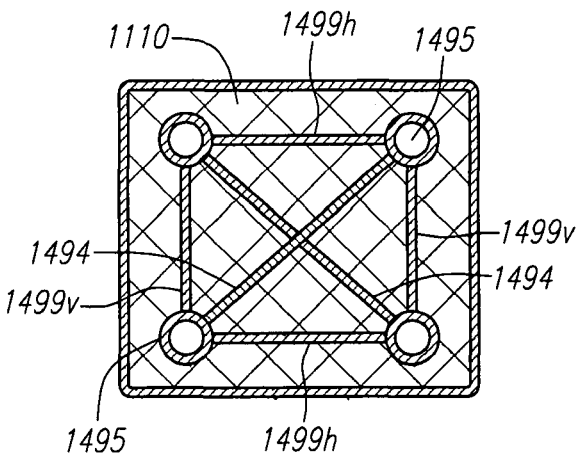
FIG. 19  FIG. 20
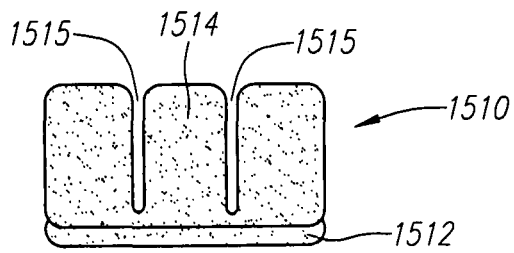 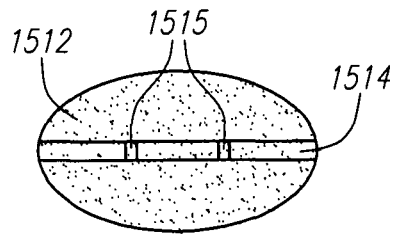
FIG. 21A  FIG. 21B
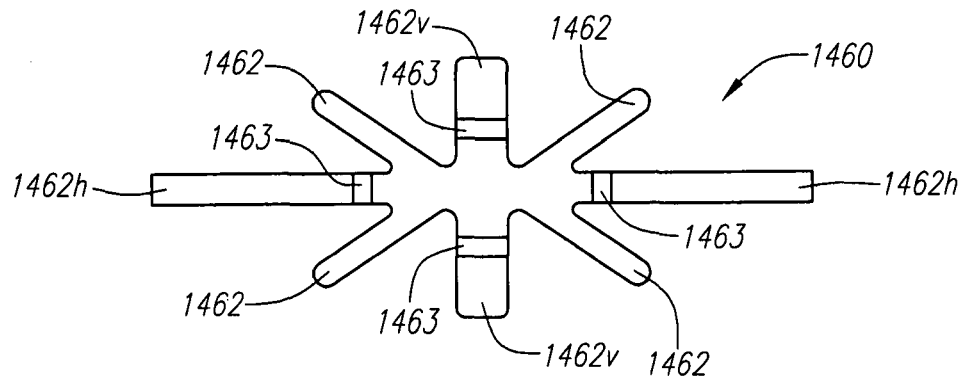
FIG. 22A
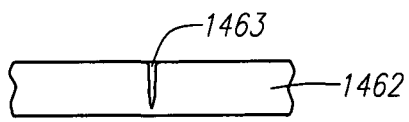
FIG. 22B

DEVICES FOR DISC HERNIATION REPAIR AND METHODS OF USE

RELATED APPLICATIONS

This application claims the benefit of U.S. Provisional Application Ser. No. 60/813,232, entitled "Devices for Disc Herniation Repair and Methods of Use", filed Jun. 13, 2006, and 60/847,649, entitled "Anulus Repair Device," filed Sep. 26, 2006, all of which are hereby expressly incorporated by reference in their entirety.

BACKGROUND

The human intervertebral disc is an oval to kidney bean-shaped structure of variable size depending on the location in the spine. The outer portion of the disc is known as the anulus fibrosus (AF). The anulus fibrosus is formed of approximately 10 to 60 fibrous bands or layers. The fibers in the bands alternate their direction of orientation by about 30 degrees between each band. The orientation serves to control vertebral motion (one half of the bands tighten to check motion when the vertebra above or below the disc are turned in either direction).

The anulus fibrosus contains the nucleus pulposus (NP). The nucleus pulposus serves to transmit and dampen axial loads. A high water content (approximately 70-80%) assists the nucleus in this function. The water content has a diurnal variation. The nucleus imbibes water while a person lies recumbent. Nuclear material removed from the body and placed into water will imbibe water swelling to several times its normal size. Activity squeezes fluid from the disc. The nucleus comprises roughly 50% of the entire disc. The nucleus contains cells (chondrocytes and fibrocytes) and proteoglycans (chondroitin sulfate and keratin sulfate). The cell density in the nucleus is on the order of 4,000 cells per microliter.

The intervertebral disc changes or "degenerates" with age. As a person ages, the water content of the disc falls from approximately 85% at birth to approximately 70% in the elderly. The ratio of chondroitin sulfate to keratin sulfate decreases with age, while the ratio of chondroitin 6 sulfate to chondroitin 4 sulfate increases with age. The distinction between the anulus and the nucleus decreases with age. Generally disc degeneration is painless.

Premature or accelerated disc degeneration is known as degenerative disc disease. A large portion of patients suffering from chronic low back pain are thought to have this condition. As the disc degenerates, the nucleus and anulus functions are compromised. The nucleus becomes thinner and less able to handle compression loads. The anulus fibers become redundant as the nucleus shrinks. The redundant annular fibers are less effective in controlling vertebral motion. This disc pathology can result in: 1) bulging of the anulus into the spinal cord or nerves; 2) narrowing of the space between the vertebra where the nerves exit; 3) tears of the anulus as abnormal loads are transmitted to the anulus and the anulus is subjected to excessive motion between vertebra; and 4) disc herniation or extrusion of the nucleus through complete anular tears.

Current surgical treatments for disc degeneration are destructive. One group of procedures, which includes lumbar discectomy, removes the nucleus or a portion of the nucleus. A second group of procedures destroy nuclear material. This group includes Chymopapin (an enzyme) injection, laser discectomy, and thermal therapy (heat treatment to denature proteins). The first two groups of procedures compromise the treated disc. A third group, which includes spinal fusion procedures, either remove the disc or the disc's function by connecting two or more vertebra together with bone. Fusion procedures transmit additional stress to the adjacent discs, which results in premature disc degeneration of the adjacent discs. These destructive procedures lead to acceleration of disc degeneration.

Prosthetic disc replacement offers many advantages. The prosthetic disc attempts to eliminate a patient's pain while preserving the disc's function. Current prosthetic disc implants either replace the nucleus or replace both the nucleus and the anulus. Both types of current procedures remove the degenerated disc component to allow room for the prosthetic component. Although the use of resilient materials has been proposed, the need remains for further improvements in the way in which prosthetic components are incorporated into the disc space to ensure strength and longevity. Such improvements are necessary, since the prosthesis may be subjected to 100,000,000 compression cycles over the life of the implant.

Current nucleus replacements (NRs) may cause lower back pain if too much pressure is applied to the anulus fibrosus. As discussed in co-pending U.S. patent application Ser. No. 10/407,554 and U.S. Pat. No. 6,878,167, the content of each being expressly incorporated herein by reference in their entirety, the posterior portion of the anulus fibrosus has abundant pain fibers.

Herniated nucleus pulposus (HNP) occurs from tears in the anulus fibrosus. The herniated nucleus pulposus often applies pressure on the nerves or spinal cord. Compressed nerves cause back and leg or arm pain. Although a patient's symptoms result primarily from pressure by the nucleus pulposus, the primary pathology lies in the anulus fibrosus.

Surgery for herniated nucleus pulposus, known as microlumbar discectomy (MLD), only addresses the nucleus pulposus. The opening in the anulus fibrosus is enlarged during surgery, further weakening the anulus fibrosus. Surgeons also remove generous amounts of the nucleus pulposus to reduce the risk of extruding additional pieces of nucleus pulposus through the defect in the anulus fibrosus. Although microlumbar discectomy decreases or eliminates a patient's leg or arm pain, the procedure damages weakened discs.

SUMMARY

The subject invention resides in methods and apparatus for treating disc herniation, which may be defined as the escape of nucleus pulposus (NP) through a void or defect in the anulus fibrosus (AF) of a spinal disc situated between upper and lower vertebra. The invention is particularly well suited to the minimization and prevention of recurrent disc herniation, in which case the defect is a hole or void which remains in the anulus fibrosus following disc operations involving partial discectomy.

The subject invention also resides in methods and apparatus for treating disc herniation, which may be defined as the escape of nucleus pulposus (NP) through a void or defect in the anulus fibrosus (AF) of a spinal disc situated between upper and lower vertebra. The invention is particularly well suited to the minimization and prevention of recurrent disc herniation, in which case the defect is a hole or void which remains in the anulus fibrosus following disc operations involving partial discectomy. The invention may be used to retain material that has been added to the disc. For example, the invention may be used to retain nucleus replacement devices, bone graft material, or other prosthetic devices.

Materials could be placed into the defective region or regions of the Anulus Fibrosus (AF) to promote healing across the entire thickness of the defective region of the AF. For example, a clot of blood marrow aspirated from the vertebrae or other bone in the skeleton could be injected into and over the defective region of the AF. The marrow aspirate could also be injected into and over the in-growth mesh patch or sheet. The cells of the marrow aspirate could be concentrated using such systems as the "Harvest Select" system by DePuy spine. Alternative materials, such as fibrin glue ("Tisseal", Baxter), or other bio-glue could be inserted into and/or over the defective region of the AF. Portions of the vertebrae near the defective region of the AF, could be perforated, for example with a 1-2 mm diameter drill bit or bur, to improve the blood supply to the relatively avascular AF. The holes are preferably drilled through the vertebral endplates (VEPs) near the defective region of the AF.

The invention may seal the defective region of the AF to promote healing on one side of the device and to prevent anti-adhesion materials from entering the defective region of the AF. Additionally, anti-adhesion materials such Coseal (Baxter) could be injected over the device.

In one embodiment, the invention is a device for fixing a defect in the anulus fibrosus of a patient. The device includes a body adapted for insertion into the defect, a mesh patch, first and second sutures, and first and second anchors. Each of the first and second sutures have a first end and a second end, the first end adapted for coupling to the mesh patch. The first and second anchors each have a first portion adapted for insertion into a bone and a second portion having an opening. The opening of the first anchor is adapted to receive the first suture and the opening of the second anchor is adapted to receive the second suture. The device may optionally include third and fourth anchors similar to the first and second anchors described above.

In another embodiment, the invention includes a method of treating a defect in a vertebral disc of a patient using the device described above. The method includes providing a body adapted for insertion into the defect, a mesh patch, first and second sutures, and first and second anchors. Each of the first and second sutures has a first end and a second end, the first end capable of being coupled to the mesh patch. The first and second anchors each have a first portion adapted to be inserted into a bone and a second portion having an opening. The first suture is threaded through the opening of the first anchor and the second suture is threaded through the opening of the second anchor. The body is inserted into the defect. The first portion of the first anchor is inserted into a vertebra cranial to the vertebral disc and the first portion of the second anchor is inserted into a vertebra caudal to the vertebral disc. The first ends of the first and second sutures are attached to the mesh patch. The mesh patch is positioned then adjacent the defect by pulling on the second end of the first and second sutures.

In another embodiment, the invention includes a method of treating a defect in a vertebral disc of a patient. A body adapted for insertion into the defect, a mesh patch coupled to the body, first and second sutures, and first and second anchors are provided. Each of the first and second sutures have a first end and a second end, wherein the first end is capable of being coupled to the mesh patch. Each of the first and second anchors have a first portion adapted to be inserted into a bone and a second portion having an opening. The first suture is threaded through the opening of the first anchor and the second suture is threaded through the opening of the second anchor. The body is inserted into the defect such that the mesh patch is positioned adjacent the defect. The first portion of the first anchor is inserted into a vertebra cranial to the vertebral disc and the first portion of the second anchor is inserted into a vertebra caudal to the vertebral disc. The first ends of the first and second sutures are attached to the mesh patch. The second ends of the first and second sutures are then pulled or otherwise put under tension.

In yet another embodiment, the invention also includes a device for fixing a defect in the anulus fibrosus of a patient. The device includes a mesh patch, a first suture assembly, and a second suture assembly. The first suture assembly includes a first anchor and a first suture. The first anchor has a first portion adapted to be inserted into a bone and a second portion having an opening therethrough. The first suture has a first end portion that is visibly distinguishable from a second end portion. The first suture is disposed through the hole in the first anchor. The second suture assembly includes a second anchor and a second suture. The second anchor has a first portion adapted to be inserted into a bone and a second portion having an opening therethrough. The second suture has a first end portion that is visibly distinguishable from a second end portion. The second suture is disposed through the hole in the second anchor.

In another embodiment, the invention also includes a method for treating a defect in a vertebral disc of a patient. The steps include providing a device including a mesh patch, a first suture assembly, and a second suture assembly. The first suture assembly includes a first anchor and a first suture. The first anchor has a first portion adapted to be inserted into a bone and a second portion having an opening therethrough. The first suture has a first end portion that is visibly distinguishable from a second end portion and is disposed through the hole in the first anchor. The second suture assembly includes a second anchor and a second suture. The second anchor has a first portion adapted to be inserted into a bone and a second portion having an opening therethrough. The second suture has a first end portion that is visibly distinguishable from a second end portion and is disposed through the hole in the second anchor. The first portion of the first anchor is inserted into a vertebra cranial to the vertebral disc. The first portion of the second anchor is inserted into a vertebra caudal to the vertebral disc. A first end of the first suture and a first end of the second suture are attached to the mesh patch. The mesh patch is positioned adjacent the defect by pulling on the second ends of the first and second sutures. The second end of the first suture and a second end of the second suture are then anchored.

In another embodiment, the invention includes a device for fixing a defect in the anulus fibrosus of a patient. The device includes a mesh patch; first, second, third, and fourth sutures; and first, second, third, and fourth anchors. The first, second, third, and fourth sutures each have a first end portion that is visibly distinguishable from a second end portion. The first, second, third, and fourth anchors each have a first portion adapted for insertion into a bone and a second portion having an opening. The openings of the first, second, third, and fourth anchors are adapted to receive the first, second, third, and fourth sutures, respectively.

In another embodiment, the invention includes a method of treating a defect in a vertebral disc of a patient. A device is provided that includes a mesh patch; first, second, third, and fourth sutures; and first, second, third, and fourth anchors. The first, second, third, and fourth sutures each have a first end that is visibly distinguishable from a second end. The first, second, third, and fourth anchors each have a first portion adapted for insertion into a bone and a second portion having an opening. The first, second, third, and fourth sutures are disposed through the openings of the first, second, third, and fourth anchors, respectively. The first portions of the first and second anchors are inserted into a vertebra cranial to the vertebral disc. The first portions of the third and fourth anchors are inserted into a vertebra caudal to the vertebral disc. A first end of the first suture and a first end of the third suture are attached to the mesh patch. A first end of the second suture and a first end of the fourth suture are attached to the mesh patch. The mesh patch is then positioned adjacent the defect by pulling on the second end portions of the first, second, third, and fourth sutures. A second end of the first, second, third, and fourth sutures are then anchored.

In yet another embodiment, the invention includes a method of treating a defect in a vertebral disc of a patient. A device is provided that includes a mesh patch; first, second, third, and fourth sutures; and first, second, third, and fourth anchors. The first, second, third, and fourth sutures each have a first end and a second end. The first, second, third, and fourth anchors each have a first portion adapted for insertion into a bone and a second portion having an opening. The first, second, third, and fourth sutures are disposed through the openings of the first, second, third, and fourth anchors, respectively. The first portions of the first and second anchors are inserted into a vertebra cranial to the vertebral disc. The first portions of the third and fourth anchors are inserted into a vertebra caudal to the vertebral disc. The mesh patch is positioned adjacent the defect. A first end of the first suture is attached to a first end of the third suture. A first end of the second suture is attached to a first end of the fourth suture. Second ends of each of the first, second, third, and fourth sutures are then anchored.

The attaching/anchoring in any of the methods described above can be accomplished in many ways. The first and/or second ends of the various sutures could be anchored either by attaching the end to another suture or by attaching the end to the mesh patch. For example, the second end of the first and second sutures could be anchored (e.g., through welding or crimping) to the second ends of the third and fourth sutures, respectively. The second end of the first suture could similarly be anchored to the second end of the second suture. The first or second ends of the sutures could also be anchored by attaching the ends to the mesh patch.

BRIEF DESCRIPTION OF THE FIGURES

FIG. 16A is a posterior view of an alternative mesh patch with a reinforcement band coursing through or over the mesh patch.

FIG. 16B is a posterior view of the mesh patch of FIG. 16A with the fixation sutures passing through the mesh and through the central portion of the high tensile strength loop.

FIG. 17A is a posterior view of an alternative mesh patch with reinforcing members or bands course through the mesh.

FIG. 17B is a posterior view of the alternative mesh patch of FIG. 17A where sutures with enlarged ends of the fixation members were placed through the openings in the reinforced regions of the mesh.

FIG. 18A is a posterior view of an alternative mesh patch having a closed loop as a reinforcement component.

FIG. 18B is a posterior view of the embodiment of the invention drawn in FIG. 18A wherein fixation members have been welded or otherwise attached to the strands of the reinforcement component.

FIG. 19 is a posterior view of an alternative mesh patch where the periphery of the mesh is reinforced with reinforcement members.

FIG. 20 is a posterior view of an alternative mesh patch where the reinforcement members have openings, and vertical, horizontal, and diagonal components.

FIG. 21A is a lateral view of an alternative suture holding device having two slots to receive sutures.

FIG. 21B is a view of the top of the embodiment of the invention drawn in FIG. 21A, FIG. 22A is a posterior view of an alternative weldable component having slots that make the device more flexible in one direction.

FIG. 22B is a lateral view of a portion of the embodiment of the invention drawn in FIG. 22A.

DETAILED DESCRIPTION

Figure 1A:
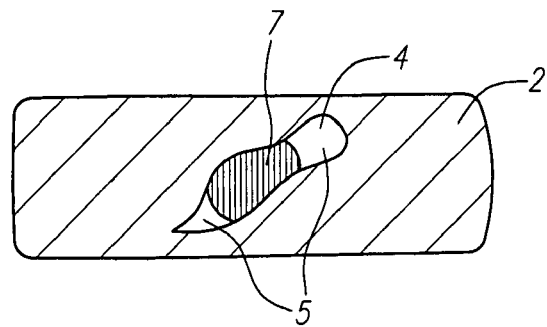
FIG. 1A is a posterior view of an intervertebral disc and with a device (or body) visible through the aperture.

FIG. 1A is a posterior view of intervertebral disc 2 and an alternative embodiment of the invention. Disc 2 has crescent shaped aperture 4. The end of a novel device (or body) 7 is seen within aperture 4. In one embodiment, body 7 does not fill the aperture. The space 5 between body 7 and the AF allows fluids, cells, tissue (including NP), or other materials to flow into and out of disc 2. Extrusion of NP tissue may facilitate healing of the damaged AF. The extruded NP provides cells and a diffusion pathway for oxygen and nutrients. Body 7 could be made of materials that promote healing of the damaged AF. For example, body 7 could be made of cells, extracellular matrix, cytokines, and other therapeutic substances. The cells could include mesenchymal stems cells, fibroblasts, fibrocytes, cartilage cells, cells harvested from the AF or the NP, or other autograft, allograft, or xenograft cells. The cells could be expanded by tissue culture. The extracellular matrix could include collagen scaffolds, and scaffolds made from autograft, allograft, or xenograft tissues. The cytokines could, include Bone Morphogenic Proteins (BMP1, BMP2, BMP3, BMP4, BMP5, BMP6, BMP7, BMP8, BMP9, BMP10, BMP11, BMP12, BMP13, BMP14, BMP15, BMP16, BMP17, . . . BMP-n), Recombinant growth hormone (rhGH) (Genetech, San Francisco, Calif.), Vascular endothelial growth factor (rhVEGF) (Genetech, San Francisco, Calif.), Platelet derived growth factor (rhPDGF-AA & rhPDGF-BB) (Chiron, Emeryville, Calif. & Amgen, Thousand Oaks, Calif.), Transforming growth factor-beta (rhTGF-Beta) (Oncogen Corp, Seattle, Wash., New England Nuclear Boston, Mass., R&D Systems, Minneapolis, Minn., & Amgen, Thousand Oaks, Calif.), Fibroblastic growth factor (rhaFGF & rhbFGF) (Amgen, Thousand Oaks, Calif. & Chiron, Emeryville, Calif.), Insulin-like growth factor (rhIGF-1) (UBI Lake Placid, N.Y. & Amgen, Thousand Oaks, Calif.), Granulocyte colony stimulating factor (rhGM-CSF, rhG-CSF) (Amgen, Thousand Oaks, Calif.), Macrophage colony stimulating factor (rhM-CSF) (Chiron, Emeryville, Calif.), and Epidermal growth factor (rhEGF) (Chiron, Emeryville, Calif.).

For example, an absorbable collagen sponge (Integra Life Sciences, Plainsboro, N.J.) could be soaked in a 1.5 mg rhBMP-2/ml sterile saline solution (Medtronic Sofamor Danek, Memphis, Tenn.) for about 15 minutes before inserting the BMP impregnated sponge into the disc. Other doses of BMP are acceptable. For example, doses from about 0.04 micrograms to about 32 mg of BMP, alternatively from about 0.1 micrograms to about 30 mg of BMP, alternatively from about 1.0 micrograms to about 25 mg of BMP, alternatively from about 5.0 micrograms to about 20 mg of BMP, could be used. Alternatively, at least about 0.04 micrograms of BMP, alternatively at least about 0.1 micrograms, alternatively at least about 0.5 micrograms, alternatively at least about 1.0 micrograms, alternatively at least about 5.0 micrograms, alternatively at least about 10.0 micrograms, alternatively at least about 50.0 micrograms, alternatively at least about 100 micrograms, alternatively at least about 500 micrograms, alternatively at least about 1.0 mg, alternatively at least about 5.0 mg, alternatively at least about 10.0 mg, alternatively at least about 15.0 mg, alternatively at least about 20.0 mg, alternatively at least about 25.0 mg, alternatively at least about 30.0 mg, alternatively at least about 35.0 mg, alternatively at least about 40.0 mg, could be used. Other synthetic and natural carriers are acceptable, such as a polyactic/polyglycolic acid sponge as mentioned in the parent app. Examples include natural polymers of collagen, hyaluronans, chitosan, alignate, and other animal or plant-derived polysaccharides. Examples of synthetic polymers include poly(alpha-hydroxy acids) such as polylactide, polyglycolide, and their copolymers, polyanhydrides, polyphosphazenes, polypropylene fumarate, polyethylene glycol-polylactic acid (PLA), poloxamers, and polyphosphate polymers. Composites of natural materials, synthetic materials, or natural and synthetic materials could also be used as carriers. For example, composites of hyaluronan-impregnated PLA sponges, collagen-PLG-alginate, and PLGA-gelatin could be used.

Figure 1B:
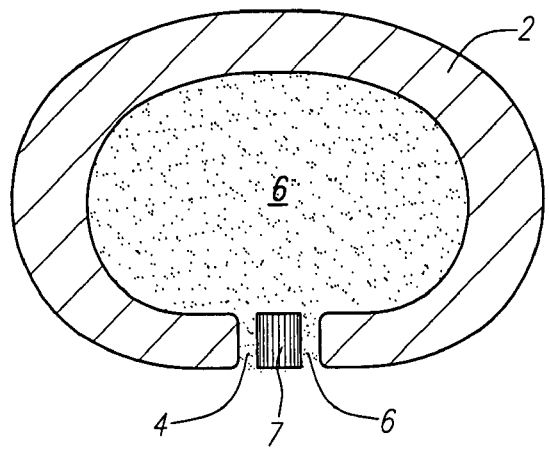
FIG. 1B is an axial cross section of an intervertebral disc and the embodiment of the invention drawn in FIG. 1A.

FIG. 1B is an axial cross section of intervertebral disc 2 and the embodiment of the invention drawn in FIG. 1A. NP 6 has extruded between body 7 and the AF.

Figure 1C:
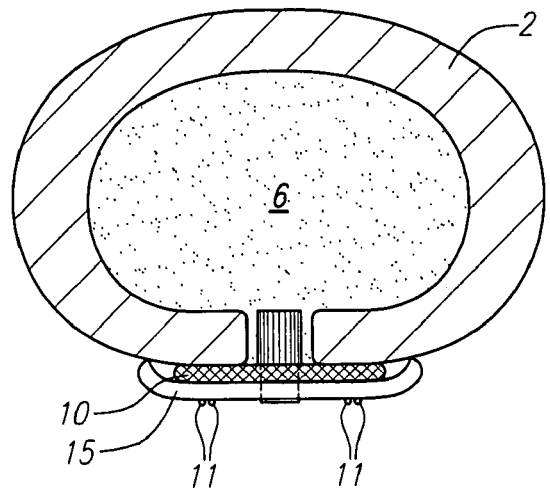
FIG. 1C is an axial cross section of the intervertebral disc with the device (or body) combined with a patch coupled to the outside of the AF to help prevent extrusion of the NP past the outer layer of the AF.

FIG. 1C is an axial cross section of intervertebral disc 2 with body 7 combined with a patch coupled to the outside of the AF to help prevent extrusion of the NP past the outer layer of the AF. The patch device is described in related U.S. Patent Application No. 60/808,795, filed May 26, 2006, entitled "Fastening Assemblies for Disc Herniation Repair and Methods of Use," 60/748,518, filed Dec. 8, 2005, entitled "Cemented Sutures" and 60/738,833, filed Nov. 21, 2005, entitled "Sub-PLL Annular Repair Methods and Devices," all of which are hereby incorporated by reference in their entirety. Mesh patch 10 prevents the NP from extruding beyond the AF. NP that extrudes beyond the disc can damage nerves. Cross sections of anti-adhesion cover 15 and sutures 11 can be seen covering mesh patch 10. Mesh patch 10 may be used to contain body 7 that is positioned or placed into aperture of or defect 4 of the AF.

Figure 2A:
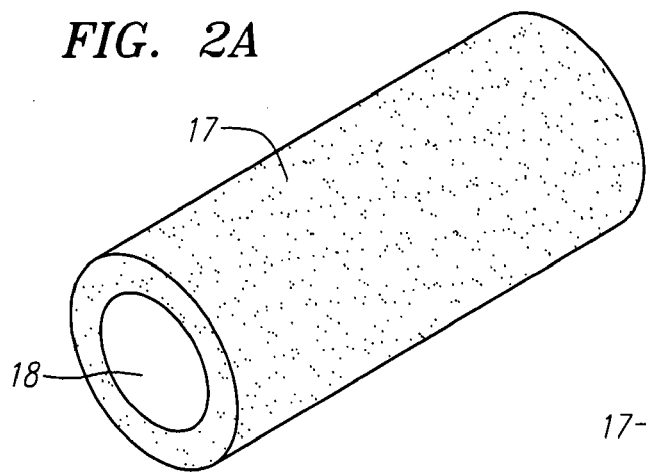
FIG. 2A is an oblique view of a tubular body adapted for insertion into an aperture in a disc.

FIG. 2A is an oblique view of an alternative embodiment of the invention drawn in FIG. 1A. Tubular body 17 provides a passageway or lumen 18 for NP material to pass into and/or through an aperture in the AF. Tubular body 17 is preferably made of resorbable materials. Suitable bio-resorbable materials include, but are not limited to, polylactic acid (PLA), polyglycolic acid (PGA), poly (ortho esters), poly(glycolide-co-trimethylene carbonate), poly-L-lactide-co-6-caprolactone, polyanhydrides, poly-n-dioxanone, and poly(PHB-hydroxyvaleric acid). Alternatively, tubular body 17 could be made of non-absorbable materials. For example, the device could be made of titanium or polyethylene.

Figure 2B:
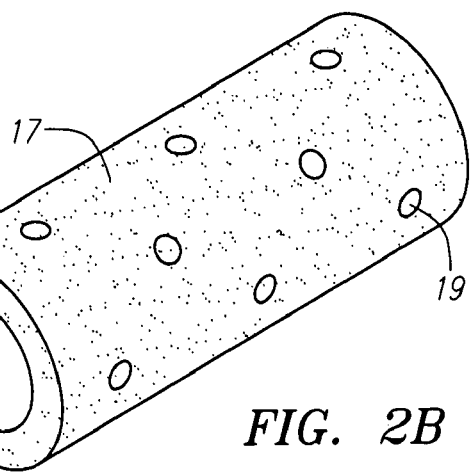
FIG. 2B is an oblique view of a tubular body made of porous material.

FIG. 2B is an oblique view of an alternative embodiment of the invention drawn in FIG. 2A. Tubular body 17 is made of porous material. Passageway or lumen 18 still allows for NP material to pass into and/or therethrough. Additionally, tubular body 17 contains pores 19 that also allow for NP material to pass into and/or therethrough. For example, tubular body 17 could be made of polypropylene, polyester, titanium, or other porous material.

Figure 2C:
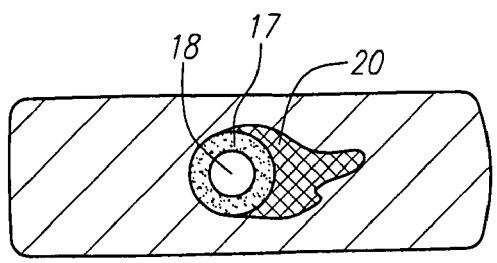
FIG. 2C is a posterior view of a disc, a tubular body, and a second porous device inserted into an aperture of a disc.

FIG. 2C is a posterior view of a disc, the embodiment of tubular body 17 drawn in FIGS. 2A and 2B, and a second porous device 20 such as a collagen sponge (area of the drawing with crossing diagonal lines). The embodiment of the device drawn in FIGS. 2A and 2B and the second porous device are located in an aperture within the disc. Lumen 18 provides a passageway for NP tissue. The additional porous device 20 does not permit migration of NP tissue. For example, the pores in the additional porous device 20 may be too small to permit NP tissue to migrate through the device.

Figure 2D:
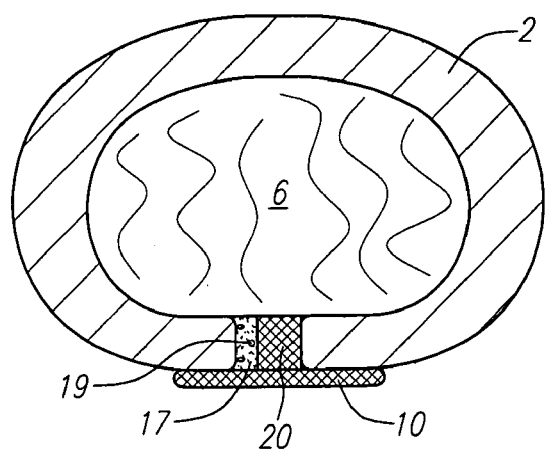
FIG. 2D is an axial cross section of a disc, the embodiments of the invention drawn in FIG. 2C, and a mesh patch.

FIG. 2D is an axial cross section of a disc 2, the embodiments of the invention drawn in FIG. 2C, and a mesh patch. Tubular body 17 and additional porous device 20 within the aperture of the disc promote healing of the AF through the aperture. Mesh patch 10 contains the NP tissue that passes through lumen 18 of tubular device 17. Mesh patch also contains tubular body 17 and additional porous device 20 within the aperture of disc 2 and promotes tissue growth across the aperture.

Figure 3A:
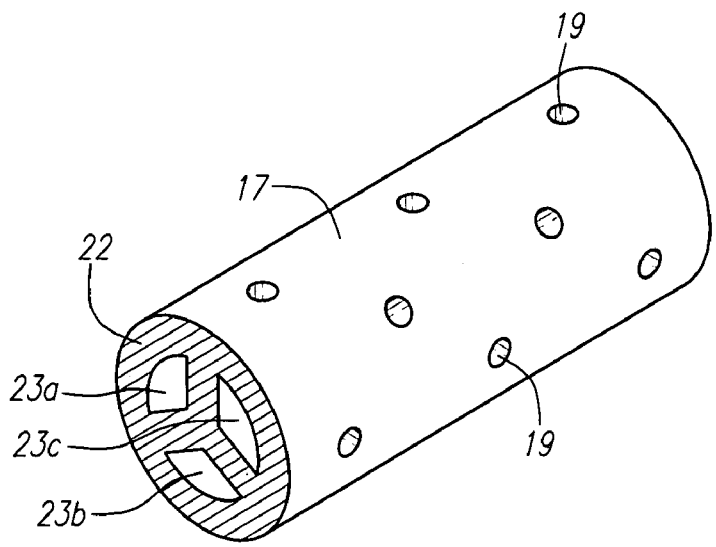
FIG. 3A is an oblique view of an alternative tubular body having a porous barrier that crosses the lumen of the tubular body.

FIG. 3A is an oblique view of an alternative embodiment of the invention drawn in FIGS. 2A and 2B. Porous barrier 22 crosses the lumen of tubular body 17. Porous barrier 22 may be located at least one of a proximal end, distal end, and/or within the lumen between the proximal and distal end of tubular body 17. Numerous porous barriers may also be positioned at the ends of or within the tubular body. Pores 19 of tubular body 17 and openings/pores 23a-c in porous barrier 22 permit small pieces of NP to migrate from the disc. Porous barrier 22 prevents large particles of NP tissue from extruding from the disc. Large particles that extrude into the spinal canal can impinge against the nerves. Small particles of extruded NP are unlikely to compress the nerves. Porous barrier 22 may be a septum, filter, membrane, or other porous structure.

Figure 3B:
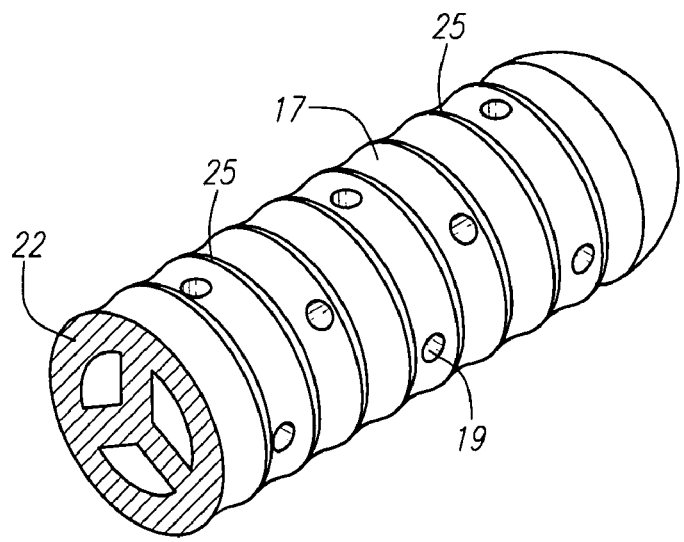
FIG. 3B is an oblique view of an alternative embodiment of the invention drawn in FIG. 3A having external threads.

FIG. 3B is an oblique view of an alternative embodiment of the invention drawn in FIG. 3A. Tubular body 17 additionally has external threads 25.

Figure 3C:
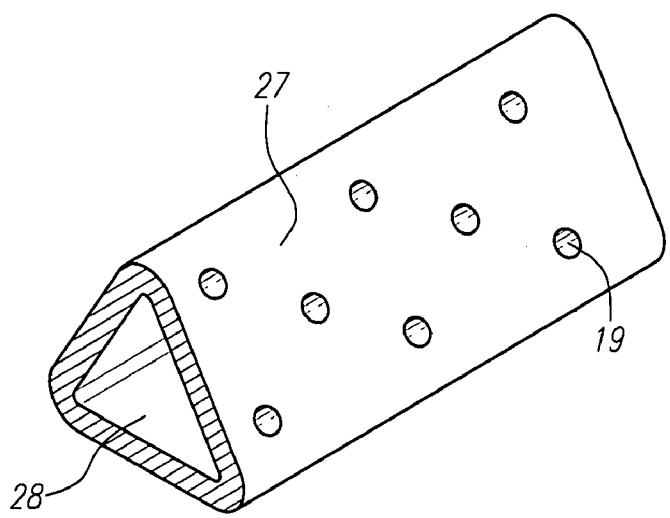
FIG. 3C is an oblique view of an alternative embodiment of the invention drawn in FIG. 3A having a triangular cross section and a triangular-shaped lumen passing therethrough.

FIG. 3C is an oblique view of an alternative embodiment of the invention drawn in FIG. 3A. The angular body 27 is triangular in cross section and has a triangular-shaped lumen 28 passing therethrough.

Figure 3D:
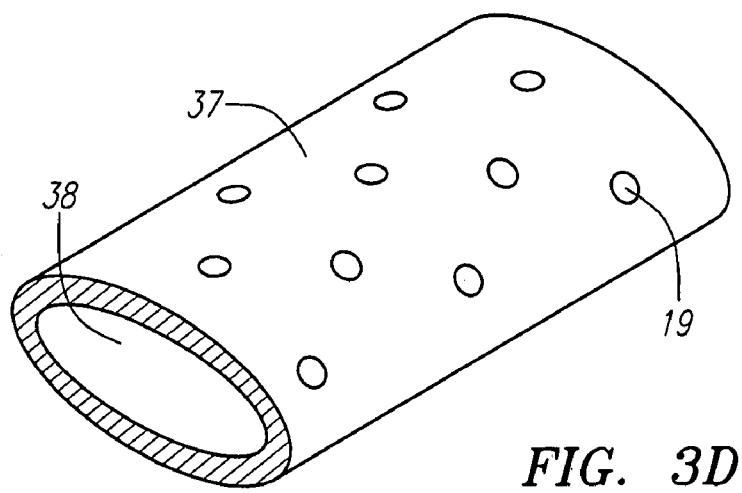
FIG. 3D is an oblique view of an alternative embodiment of the invention drawn in FIG. 3C having an oval cross section and an oval-shaped lumen passing therethrough.

FIG. 3D is an oblique view of an alternative embodiment of the invention drawn in FIG. 3C. The body 37 is oval in cross section and has an oval-shaped lumen 38 passing therethrough The device may have alternative shapes such as a square, rectangle, pentagon, hexagon, heptagon, octagon, or other polygon, ellipse, etc.

Figure 3E:
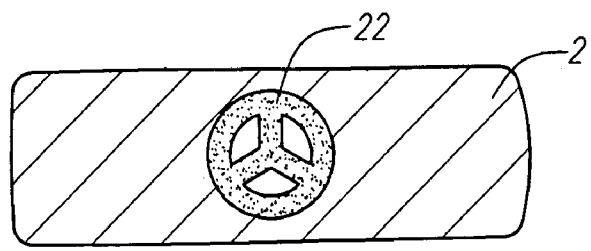
FIG. 3E is a posterior view of the disc with a tubular body inserted into the disc.

FIG. 3E is a posterior view of the disc and the embodiment of the invention drawn in FIG. 3B. Tubular body 17 has been threaded into an aperture in the AF. Tubular body 17 may form a tight seal with the AF. A natural opening in the AF may be enlarged with a cylindrical shaped trocar before inserting the device.

Figure 3F:
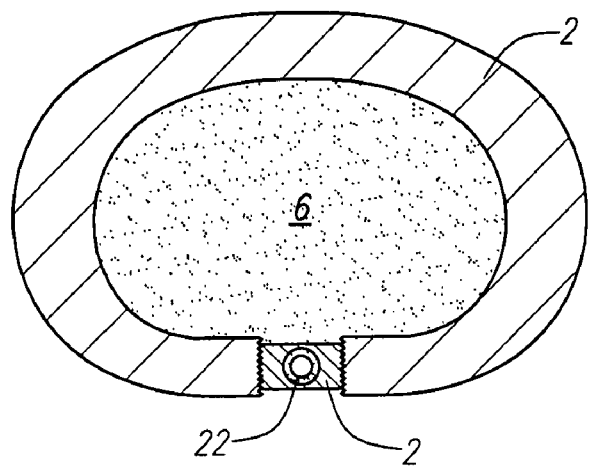
FIG. 3F is an axial cross section of the disc and the embodiment of the invention drawn in FIG. 3E, which illustrates a tubular body with a porous barrier forming a tight seal with the surrounding the anulus fibrosus of the disc.

FIG. 3F is an axial cross section of the disc and the embodiment of the invention drawn in FIG. 3E, which illustrates tubular body (not shown) with porous barrier 22 forming a tight seal with the surrounding AF of disc 2.

Figure 4A:
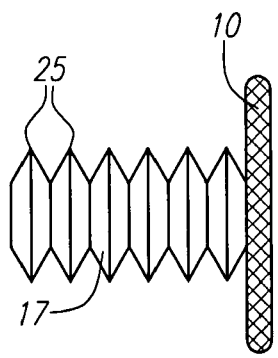
FIG. 4A is a lateral view of a tubular body with external threads that is connected or coupled to a mesh patch.

FIG. 4A is a lateral view of an alternative embodiment of the invention drawn in FIGS. 2D and 3B. The device has a tubular body 17 with external threads 25 connected or coupled to mesh patch 10. The device could made of porous mesh, collagen, allograft, xenograft, autograft, metallic, or polymer materials. Alternatively, the device may be made of more than one material.

Figure 4B:
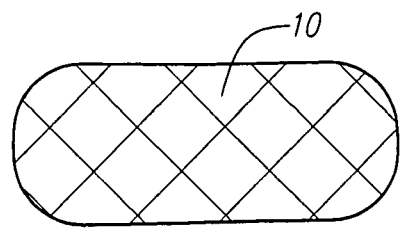
FIG. 4B is a posterior view of the embodiment of the invention drawn in FIG. 4A, showing the face of the porous mesh patch.

FIG. 4B is a posterior view of the embodiment of the invention drawn in FIG. 4A, showing the face of porous mesh patch 10.

Figure 4C:
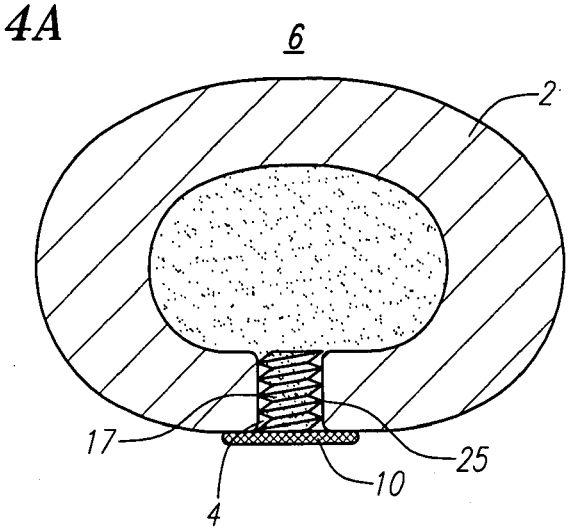
FIG. 4C is an axial cross section of a disc and the embodiment of the invention drawn in FIG. 4A.

FIG. 4C is an axial cross section of disc 2 and the embodiment of the invention drawn in FIG. 4A. Body 17 with threads 25 fits within aperture 4 of disc 2. The inner diameter of body 17 with threads 25 is smaller than the inner diameter of aperture 4. The configuration permits NP material 6 to spiral around body 17 and threads 25. Mesh patch 10 lies over the outer layer of the AF of disc 2. Mesh patch 10 of the device prevents NP 6 from extruding from disc 2. Thus, the device permits NP tissue 6 to pass into aperture 4 but not through aperture 4 of the intervertebral disc 2.

Figure 4D:
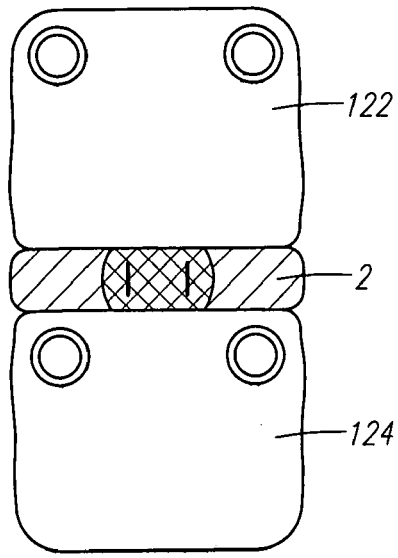
FIG. 4D is a posterior view of a sagittal cross section of the spine and the embodiment of the invention drawn in FIG. 4C.

FIG. 4D is a posterior view of a sagittal cross section of the spine and the embodiment of the invention drawn in FIG. 4C. Mesh patch 10 of the invention has been attached to the AF adjacent to aperture 4 in disc 2. Sutures or other anchors may be used to attach the device to the AF, as described in U.S. Patent Application No. 60/808,795, filed May 26, 2006, entitled "Fastening Assemblies for Disc Herniation Repair and Methods of Use," 60/748,518, filed Dec. 8, 2005, which was previously incorporated by reference. For example, flexible T-shaped anchors with a transverse component placed behind the AF and a longitudinal component the passes through the AF could be used to fasten the device to the AF.

Figure 4E:
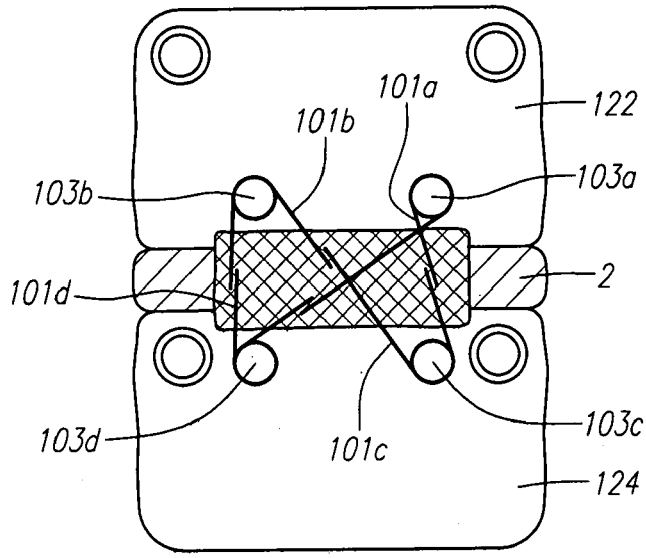
FIG. 4E is a posterior view of a sagittal cross section of the spine and a device attached to the spine with suture anchors.

FIG. 4E is a posterior view of a sagittal cross section of the spine and an alternative embodiment of the invention drawn in FIG. 4D. The device has been attached to the spine with suture anchors. Two anchors 103a-b have been inserted into the vertebra 122 cranial (towards the head) to the disc 2 and two anchors 103c-d have been inserted into the vertebra 124 caudal (towards the feet) to the disc 2. Anchor 103 has a first portion capable of being inserted into or otherwise attached to a bone, such as a vertebra. Anchor 103 also has a second portion capable of being coupled with suture 101, such as an opening adapted to receive a suture therethrough. In one embodiment, anchor 103 is a screw having a hole through the head of screw. Suture 101 is threaded through the hole. Alternatively, suture 101 may be wrapped around a portion of anchor 103. Suture 101 is preferably made of polyester or other weldable material and has a break-strength of greater than about 22 lbs. Screw or anchor 103 is preferably about 3 mm in diameter, alternatively about 4 mm in diameter, and between about 5 mm and about 10 mm in length. However, alternative sized sutures or screws may be used with this invention. Anchors 103 are preferably made of an MRI compatible and radio-opaque material such as Titanium. Plastic or bioresorbable anchors may also be used with this invention. Anchors 103 are preferably self-drilling and self-tapping: Non-threaded anchors with expandable or deployable components may also be used with this invention.

As seen in FIG. 4E, the free ends of the sutures may be attached, e.g., through welding, to each other to hold the mesh patch in place. For example, a first end of suture 101b may be welded or otherwise connected to a first end of suture 101c to form a connection diagonally across the back of the mesh patch. Similarly, a first end of suture 101a may be welded or otherwise connected to a first end of suture 101d to form another connection diagonally across the back of the mesh patch. A second end of suture 101b may be connected to a second end of suture 101d to form a generally vertical connection across the back of the mesh patch. A second end of suture 101a may be connected to a second end of suture 101c to form an additional generally vertical connection across the back of the mesh patch. Alternatively, the free ends of the sutures could be connected to form generally horizontal connections across the back of the mesh patch. The sutures may additionally or optionally be welded directly to the mesh patch. Alternatively, the free ends of the sutures could be fastened to the anchors. The anchors may have a clamp-like mechanism that locks the free ends of the sutures to the anchors. The invention fastens sutures to each other, to the mesh, or to the anchors without requiring tying knots in the sutures.

Mesh patch 10 is smaller than the area between the four anchors 103a-d. The mesh patch could be smaller than the distance between the anchors by a ratio of 4:5. For example, if the distance between the anchors in the same vertebra is about 10 mm and the distance between anchors in the adjacent vertebra is about 15 mm, a rectangular mesh patch would preferably be about 8 mm×12 mm. Alternatively, the ratio may be about 4.5:5, alternatively about 3.5:5, alternatively about 3.0:5, alternatively about 2.5:5. The size of the mesh patch could be determined by the pair of suture anchors that are closest together in the vertical and the horizontal directions. Sutures 101a-d can be welded to each other and/or to mesh patch 10 using an ultrasonic welding instrument, such as supplied by Axya Medical Beverly, Mass.

Figure 5A:
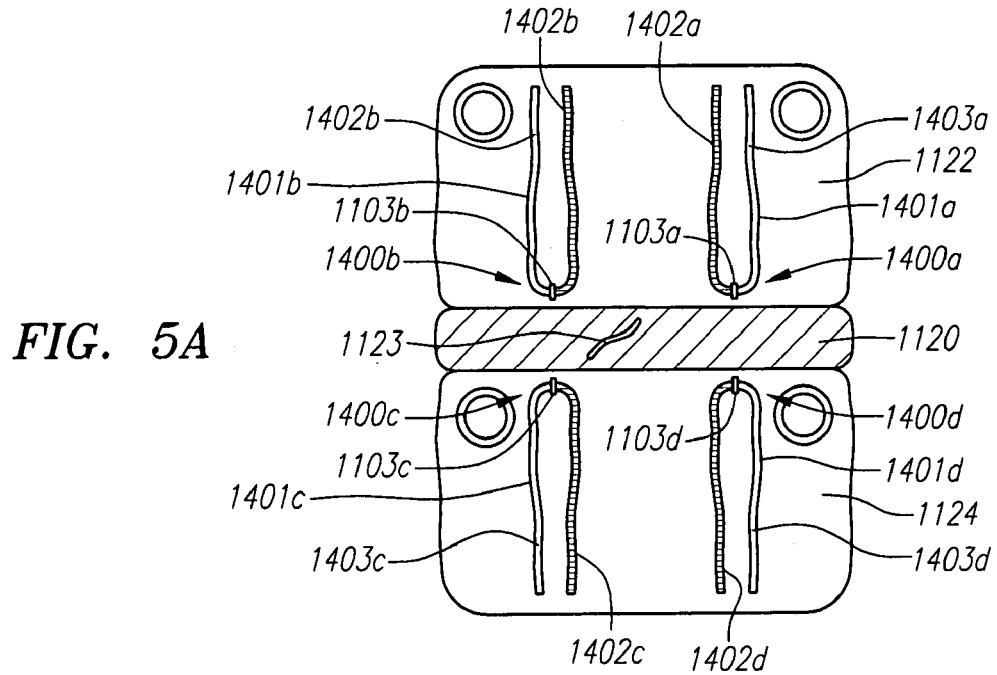
FIG. 5A is a posterior view of a coronal cross section of the spine with two anchors, with associate sutures, inserted into each of the cranial and caudal vertebrae surrounding a disc having a defect.

FIG. 5A is a posterior view of a coronal cross section of the spine and the first component of the preferred embodiment of the invention. The circles represent cross sections of the pedicles of vertebrae 1122 and 1124. Disc 1120 is the rectangular structure between vertebrae 1122 and 1124. Elongated aperture 1123 is drawn on the posterior aspect of the Anulus Fibrosus (AF) of disc 1120. Two suture anchors 1400a, b were placed in vertebra 1122 cranial to the disc and two suture anchors 1400c,d were placed in vertebra 1124 caudal to the disc. A pair of anchors is located medial to the aperture and a pair of anchors is located lateral to the anchors. The four anchors can be grouped into a pair (an anchor cranial to the disc and an anchor caudal to the disc) to the left of the aperture and a pair to the right of the aperture. The cranial pair anchors 1400a,b are preferably located at least 2 mm cranial to the junction of cranial vertebra 1122 and disc 1120. The caudal pair of anchors 1400c,d are preferably located at least 2 mm caudal to the junction of caudal vertebra 1124 and disc 1120. Alternatively, the anchors can be placed about 1 to about 15 mm cranial and about 1 to about 15 mm caudal to the junctions of the disc and the vertebrae. The anchors are also placed at least 2 mm medial and 2 mm lateral to aperture 1123 in the anulus fibrosus. Alternatively, the anchors may be placed about 1 to about 15 mm medial and lateral to aperture 1123. Sutures 401a-d are marked to identify the medial 1402a-d and the lateral 1403a-d halves of the sutures 1401a-d. For example, the medial ends 1402a-d of the sutures could be a first color and the lateral ends 1403a-d of the sutures could be a second color. Alternatively, the first ends of the sutures could have spots, stripes, bands, or other markings to differentiate the first ends from the second ends of the sutures. Multifilament sutures could incorporate colored fibers to help differentiate the medial and the lateral ends of the sutures. The suture anchors 1103a-d are preferably about 3 mm in diameter and about 7 mm in length. Alternatively, suture anchors 1103a-d may be about 2 to about 7 mm in diameter and about 4 to about 15 mm in length.

Suture anchor 1400 comprises suture 1401 and screw (or anchor) 1103. Anchor 1103 has a first portion capable of being inserted into or otherwise attached to a bone, such as a vertebra. Anchor 1103 also has a second portion with an opening 1104 adapted to receive a suture therethrough. In one embodiment, anchor 1103 is a screw having a hole through the head of screw. Suture 1401 is threaded through hole 1104. Anchors 1103a-d are preferably made of titanium, plastic, or other MRI compatible material. The anchors may be absorbable. The holes for anchors 1103a-d are preferably created with a 1.5 mm diameter drill bit and a drill guide. Alternatively, the anchors could be self-drilling and self-tapping. The handle of the instrument used to insert the anchors could have markings to identify the two ends of the fixation suture. For example, one half of a white fixation suture could be dipped in blue dye. A blue circle could be placed on the handle of the instrument used to insert the anchors. The anchors could be placed into the insertion tool with the blue end of the suture passing from the side of the instrument with the blue circle.

Figure 5B:
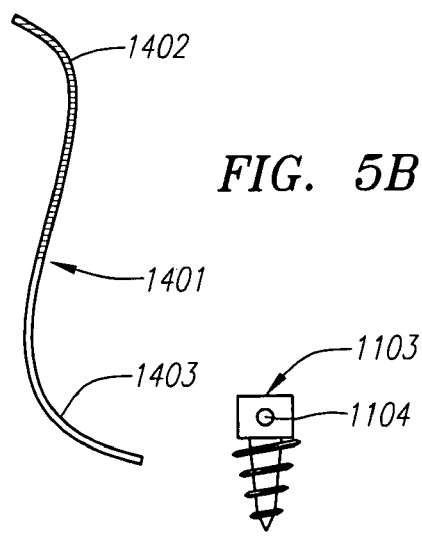
FIG. 5B is an exploded lateral view of sutures and anchors drawn in FIG. 5A.

FIG. 5B is an exploded lateral view of sutures 1401 and anchors 1103 drawn in FIG. 5A. As explained previously, suture 1401 is marked to identify the medial 1402 and the lateral 1403 halves of the suture 1401. The sutures are preferably #2 nylon or polyester sutures. Alternatively, the sutures may be made of other material. The sutures are preferably about 0.5 mm in diameter and about 90 cm in length. Alternatively the sutures are about 0.2 to about 1.0 mm in diameter and about 20 to about 110 cm or more in length. Monofilament or multifilament sutures may be used. The sutures may be made of elastic or inelastic materials. For example, the sutures may reversibly lengthen about 0.1 to about 10 mm. Alternatively, elastic sutures may reversibly lengthen about 1 to about 4 mm. Elastic sutures that are attached to anchors within the vertebrae can lengthen as the spine is moved from a neutral or and extended position to a flexed position. Elastic sutures would decrease the force on the anchors with spinal flexion. Elastic sutures would be less likely to break with repetitive spinal movement or large ranges of spinal movement. Relatively inelastic sutures may be preferred in embodiments of the invention that are used for spinal fusion.

Figure 5C:
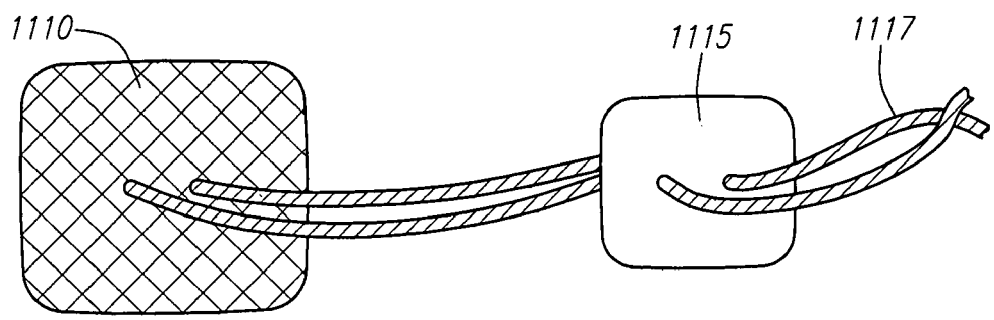
FIG. 5C is a posterior view of a mesh patch connected to an anti-adhesion patch through a suture.

The sutures or the welds are preferably designed to break at a lower force than is required to pull the anchors out of the vertebrae. The sutures or welds could be designed to break at a 30 lb force less than is required to pull the anchors out of the vertebrae. For example, AxyaLoop Ti 3.0 (Axya Medical, Beverly Mass.) suture anchors have a mean pullout force of about 77.9 pounds in cancellous bone. Such anchors could be used with #2 Fiberwire suture (Arthrex, Naples Fla.), which has a breakage strength of 44 lbs. Alternatively, the suture or suture fastening method, such as welding or clamps within the anchors, could break or release at a force approximately 70 lbs below the force required to pull the anchors out of vertebrae. For example, #5 Fiberwire suture, which has a breakage strength of about 112 lbs, could be used with Herculon suture anchors, which have a mean pullout force of 190 lbs. Alternatively, the sutures or suture fixation/fastening mechanism could be designed to break at a force less than about 10, about 20, about 30, about 40, about 50, about 60, or about 80, or between about 10 and 100 pounds or less than the force required to pull the anchors out of vertebrae. Sutures made of resorbable material, such as Vicryl, Vicryl Plus, Monocryl, or PDS II (Ethicon, Piscataway N.J.) could be used to reduce force on the anchors as the sutures resorb. The invention prevents the anchors from pulling out of the vertebrae. Extruded anchors could damage structures, such as the esophagus, that lie over the vertebrae FIG. 5C is a posterior view of patch components of the invention drawn in FIG. 5A. A mesh in-growth component 1110 is connected to an anti-adhesion component 1115 by a connecting suture 1117. Mesh component 1110 is preferably made of polyester. Mesh component 1110 is preferably about 0.25 mm thick. Alternatively, mesh component 1110 may be about 0.1 to about 2.0 mm thick. The mesh preferably has 1 by 1 mm pores. Alternatively, the mesh may have pores about 0.001 by about 0.005 mm in size to about 1 by about 3 mm in size. The holes in the mesh may be circular or elongate in shape. The mesh preferably has a burst-strength of 50 to 100 PSI. Alternatively, the mesh may have a burst-strength of 25 to 175 PSI. The mesh may be made of other synthetic materials such as polypropylene. Alternatively, the mesh may be made of processed allograft or xenograft tissue. The mesh component is preferably supplied in various sizes. For example, the mesh may be supplied in 10 by 10 mm, 12 by 14 mm, 13 by 20 mm, 14 by 18 mm, and 16 by 50 mm sizes. Alternative sizes of mesh may be supplied. The mesh may be cut by surgeons to properly fit patient's anatomy. Anti-adhesion cover 115 is preferably made of ePTFE. Alternatively, the cover may be made of other anti-adhesion materials, including absorbable materials such as, Seprafilm (Genzyme Corporation, Cambridge, Mass.), and mixtures of oxidized atelocollagen type I, polyethylene glycol, and glycerol. The anti-adhesion cover is preferably 2 mm wider and 2 mm taller than the mesh component. Alternatively, anti-adhesion cover 1115 may be the same size as the mesh patch or 3 to 15 mm wider and/or taller than the mesh patch. The cover is preferably the same shape as mesh patch 1110. Alternatively, cover 1115 may be a different shape than mesh patch 1110. For example, cover 1115 could include arms that extend from one or more sides of the cover. Cover 1115 is applied to the posterior surface of mesh component 1110. Cover 1115 is preferably connected to the patch by connecting suture 1117, e.g., a 2-0 suture. Alternatively, connecting suture 1117 may be a 4-0 to #3 suture. Connecting suture 1117 is preferably made of monofilament nylon. Alternatively, multifilament sutures made of polyester or other material, including resorbable materials may be used in other embodiments of the invention. The sutures preferably have at least a 22 lb. breakstrength. Alternatively, the sutures may have a break-strength of 10 to 140 lbs. The sutures may also be metal cables with a break strength of more than 100 lbs. For example, braided cables could be connected by crimping the ends of the cables together by a separate component, rather than by welding. Alternative fastening methods or devices may be used to connect the components. For example, adhesives could be used to connect a portion of the components together. The mesh and cover components may be made of elastic or inelastic materials. Elastic material mesh and/or cover components may reversibly lengthen about 0.1 to about 10 mm in any all directions. Alternatively the components may lengthen by about 1 to about 5 mm. The components could be more elastic in one direction than in another direction. For example, the materials could reversibly lengthen in a cranial to caudal direction more than they lengthen in a left to right direction.

Figure 5D:
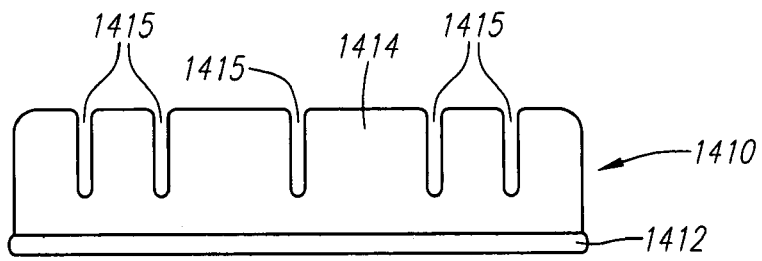
FIG. 5D is a lateral view of suture managing tool component of the invention.

FIG. 5D is a lateral view of suture managing tool component 1410 of the invention. Slots 1415 on the posterior aspect 1414 of the tool are sized to enable the fixation sutures 1401 from the anchors and the connecting sutures 1117 to be pressfit into slots 1415. The edges of the slots are rounded to avoid injuring the sutures are the sutures are repeated pressed into and pulled out of the slots. An adhesive is preferably applied to base 1412 of the tool. The tool is preferably about 2 to about 10 cm wide, about 1 to about 4 cm tall, and about 4 to about 20 cm long.

Figure 5E:
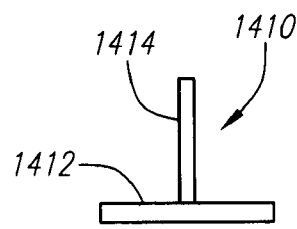
FIG. 5E is a view of the end of the embodiment of the invention drawn in FIG. 5D.

FIG. 5E is a view of the end of the embodiment of the invention drawn in FIG. 5D, which illustrates base 1412 and posterior aspect 1414 attached generally perpendicularly to base 1412.

Figure 5F:
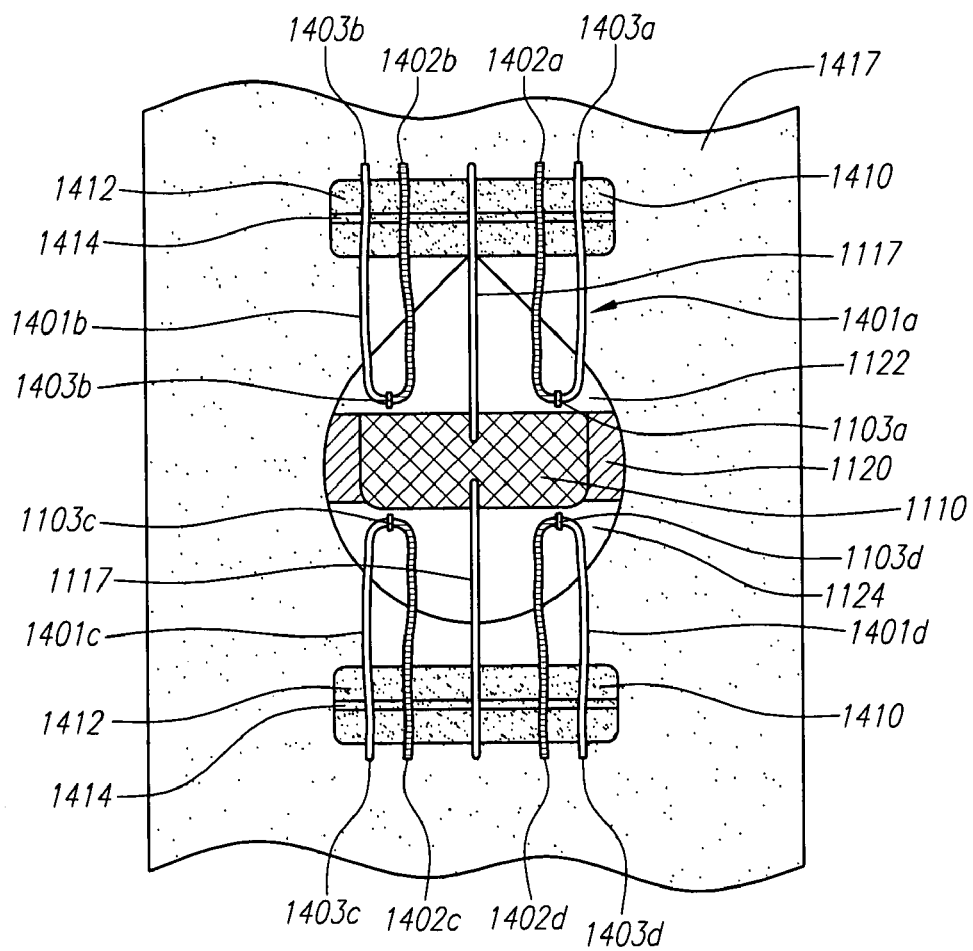
FIG. 5F is a posterior view of a portion of a patient's back, a surgical wound and the embodiments of the invention drawn in FIGS. 5A to 5E.

FIG. 5F is a posterior view of a portion of a patient's back, a surgical wound and the embodiments of the invention drawn in FIGS. 5A to 5E. Suture management tools 1410 were placed onto the patient's back cranial and caudal to the surgical wound. The adhesive on base 1412 may be used to bond the tools to the patient's skin or plastic cover 1417 over the patient's skin. The ends of the fixation sutures 14401*a-d* and the connecting sutures 1117 were press fit into slots 1415 of suture management tools 1410. The markings on the fixation sutures and the position of the sutures in the suture management tools help the surgeon identify the origin of the sutures. Anchors 1103*a-d* were preferably recessed 1 mm into the vertebrae 1122, 1124. Alternatively, the anchors may project 2 mm from the vertebrae 1122, 1124 or be recessed 2 to 10 mm into the vertebrae. Bone could grow into the holes through which the anchors were inserted (proximal to the anchors). The new bone could prevent extrusion of recessed anchors. Alternatively, as noted in U.S. application Ser. No. 11/635,829 entitled "Sutures for use in the Repair of Defects in the Anulus Fibrosus," which is hereby expressly incorporated by reference in its entirety, an in-situ curing material, such as a bioactive cement, may be injected into the bone proximal to the anchor to increase the force required to pull the anchor out of the bone. Anchors 1103 were rotated to orient the eyelet 1104 of the anchors generally parallel to disc 1120. The configuration provides a medial and a lateral end of each fixation suture. For example, as illustrated, the medial ends 1402*a-d* of the fixation sutures have small horizontal lines to differentiate the medial ends from the lateral ends 1403*a-d* of the sutures 1401*a-d*. Mesh patch 1110 is preferably 4 mm wider than the space between the medial and the lateral pairs of anchors (each pair has an anchor cranial to the disc and an anchor caudal to the disc). Alternatively mesh patch 1110 could be 1 to 10 mm wider than the space between the medial and the lateral pairs of anchors. The mesh patch is preferably as tall as the shortest distance between the pair of medial and the pair of lateral anchors. The configuration allows the mesh patch to lie against disc 120 without wrinkles in the mesh. Alternatively, the mesh patch could be wider than the distance between the medial or the lateral, or both, pairs of anchors. Alternatively, the mesh patch could be 1 to 6 mm shorter than the distance between the medial or the lateral pairs of anchors. The mesh preferably extends over the vertebrae cranial and caudal to the disc by at least 2 mm. Alternatively, the mesh could extend over the vertebrae by 1 to 10 mm. Alternatively, the mesh may extend over the disc but not the vertebrae. The cover component (not shown) is preferably added to the device at the end of the procedure.

Figure 5G:
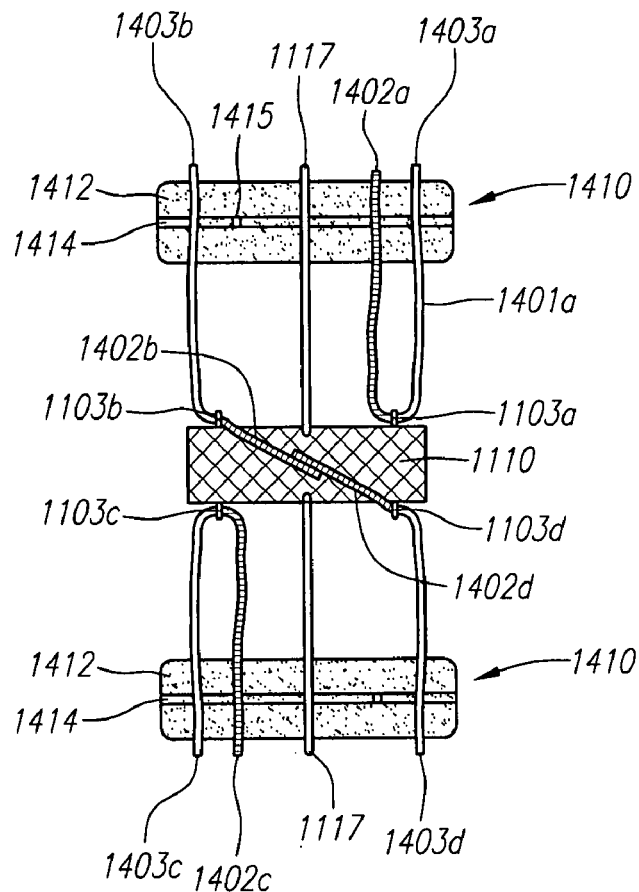
FIG. 5G is a posterior view of the embodiment of the invention drawn in FIG. 5F with the medial end of the fixation suture from the "10 o'clock" anchor welded or otherwise fastened to the medial end of the suture from the "4 o'clock" anchor.

FIG. 5G is a posterior view of the embodiment of the invention drawn in FIG. 5F. The medial end of the fixation suture from the "10 o'clock" anchor 1402*b* was welded or otherwise fastened to the medial end of the suture from the "4 o'clock" anchor 1402*d*. The welded sutures were placed between the cranial and the caudal ends of the connecting suture 1117. Tension was applied to the free ends of the welded sutures 1401 *b, d* to position the welded area of the sutures over the center of the mesh. The welded sutures hold the mesh in position over the aperture in the disc. The welding system supplied by Axya Medical (Beverly, Mass.) could be used to weld the sutures.

Figure 5H:
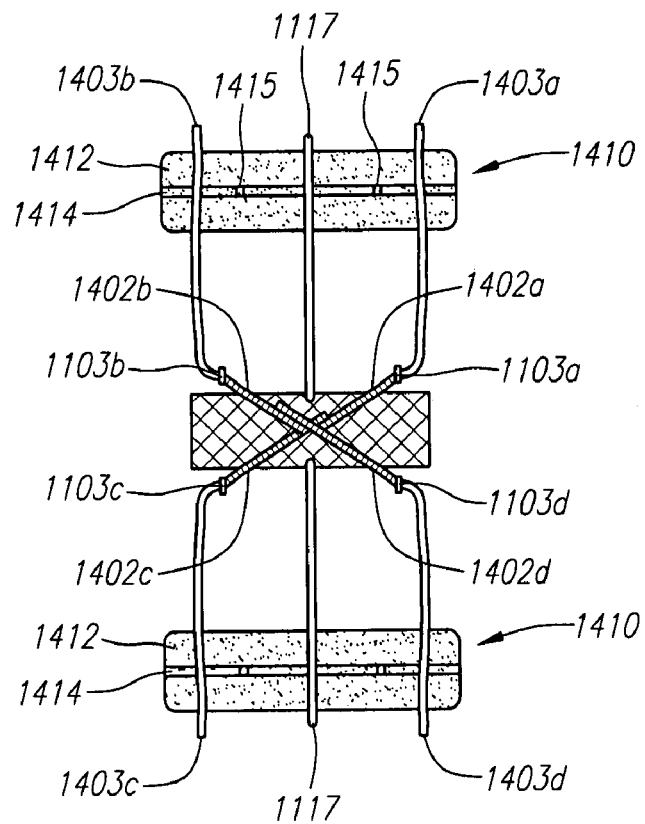
FIG. 5H is a posterior view of the embodiment of the invention drawn in FIG. 5G with the medial ends of the "2 o'clock" and the "8 o'clock" fixation sutures welded together.

FIG. 5H is a posterior view of the embodiment of the invention drawn in FIG. 5G. The medial ends of the "2 o'clock" 1402*a* and the "8 o'clock" 1402*c* fixation sutures were welded in the manner described in the text of FIG. 5G.

Figure 5I:
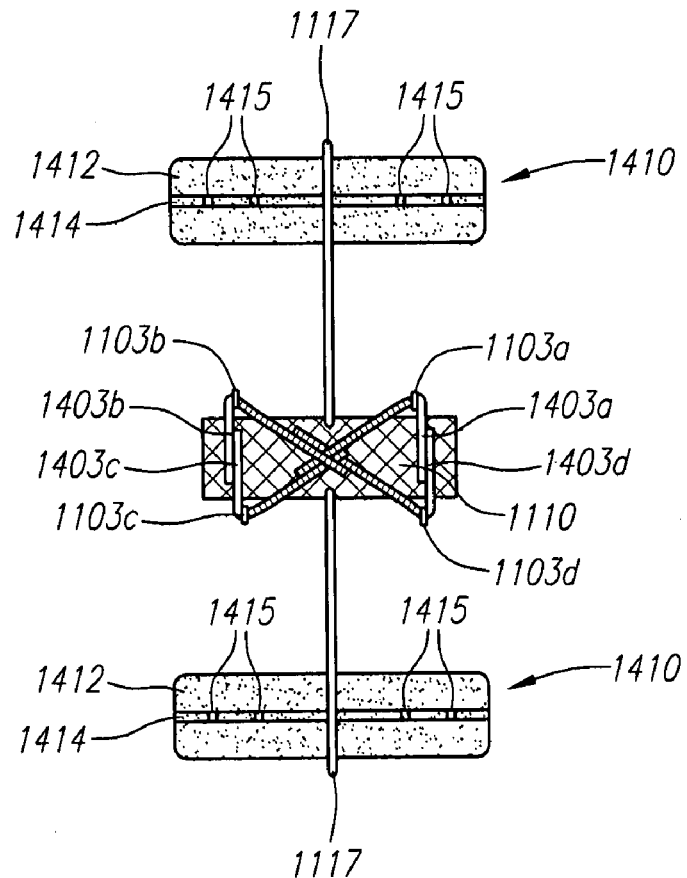
FIG. 5I is a posterior view of the embodiment of the invention drawn in FIG. 5H with the lateral ends of various sutures welded together.

FIG. 5I is a posterior view of the embodiment of the invention drawn in FIG. 5H. The lateral end of the "2 o'clock" suture 1403*a* was attached to the lateral end of the "4 o'clock" suture 1403*d*. The lateral end of the "8 o'clock" suture 1403*c* was attached to the lateral end of the "10 o'clock" suture 1403*b*. Tension was applied to the ends of the sutures before attaching the sutures. Tension on the final two pair of attached sutures, before attaching the sutures, tightens all the attached fixation sutures. The sutures may be attached by welding, crimping, or other means. By applying tension to the lateral fixation sutures before welding or otherwise attaching them, the surgeon is able to apply compression to materials, such as bone graft devices, that are placed in the intradiscal space. For example, if a piece of bone graft was placed into the intradiscal space between the vertebrae, and the surgeon compressed down on the lateral fixation sutures, the compression of the vertebrae on the bone graft could facilitate fusion. Alternatively, the sutures could be fixed to the anchors. Such configuration enables application of tension to each pair of welded sutures. For example, twenty (20) pounds of tension could be applied to the vertical pairs of sutures and eight (8) pounds of tension could be applied to the diagonal pairs of sutures. In general about 4 to about 80 pounds of tension are applied to the sutures. Smaller amounts of tension are applied to the sutures in embodiments of the invention that do not restrict spinal motion and larger amounts of tension are applied to the sutures in embodiments of the invention that are designed to restrict or eliminate movement between the vertebrae. The invention also prevents loosing of all welded sutures if a single suture breaks or a single weld fails. Mesh patch 110 should extend lateral to both pairs of attached vertical sutures. The ends of the sutures are preferably cut with guillotine-like arthroscopic suture cutter. Such cutters are the safest way to cut sutures in the spinal canal.

A device that applies compression may be used to pull the vertebrae together before the sutures are connected to one another, for example, by welding the ends of the sutures or by fastening the sutures to the anchors. For example, a distraction device, such as a Caspar distractor, could be used to force the vertebrae together before fastening the sutures. The invention helps compress intradiscal material, such as a bone graft. Such compression facilitates spinal fusion. The natural elasticity of the spinal tissues apply tension on the sutures when the external compression or "preload" is released, thus stiffening the spine. Additional tension may be applied to the sutures before welding or fastening the sutures. The compression device preferably applies at least 20 N of compression to cervical vertebrae and 400 N to lumbar vertebrae before the sutures are fastened or welded together. Alternatively, about 10, about 30, about 40, about 50 or more Newton forces ( or forces between 10-70 N) could be used to compress cervical vertebrae and about 100, about 200, about 300, about 350, about 450 or more Newton forces (or forces between 100 and 600 N) could be used to compress lumbar vertebrae together. Preoperative bone densities could be used to help select the "preload" force to apply to the vertebrae.

Figure 5J:
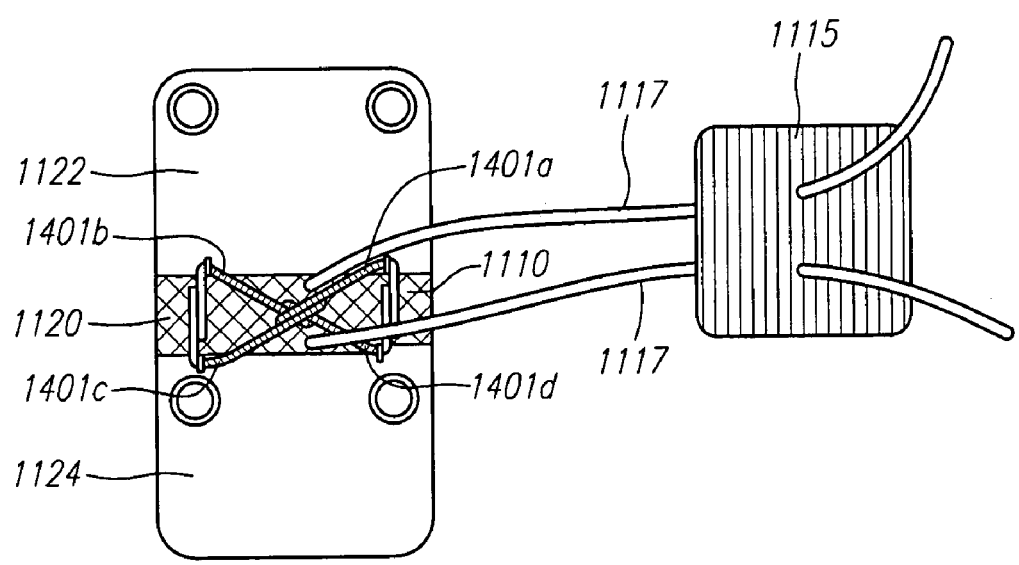
FIG. 5J is a posterior view a coronal cross section of the spine and the embodiment of the invention drawn in FIG. 5I with the suture management tools removed and an anti-adhesion cover connected through a suture.

FIG. 5J is a posterior view a coronal cross section of the spine and the embodiment of the invention drawn in FIG. 5I. The suture management tools were removed. The cover component 1115 was threaded over the ends of connecting suture 1117. Connecting suture 1117 holds mesh patch 1110 to the fixation sutures 1401*a-d* and cover component 1115 to mesh component 1110.

Figure 5K:
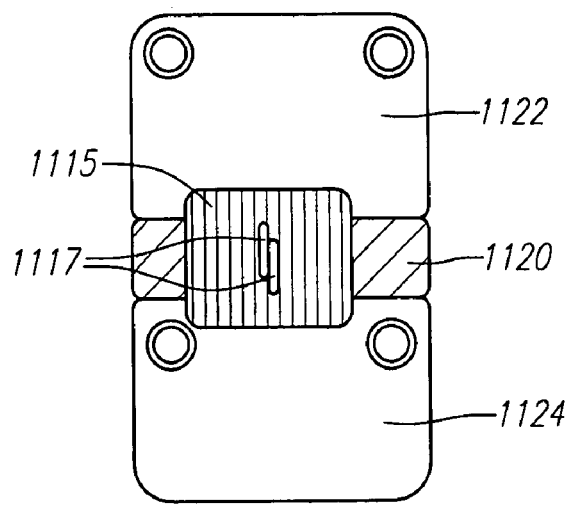
FIG. 5K is a posterior view of a coronal cross section of the spine showing the anti-adhesion cover attached by a welded suture.

FIG. 5K is a posterior view of a coronal cross section of the spine and the embodiment of the invention drawn in FIG. 5J. The ends of the connecting sutures 1117 were welded together. Tension was applied to the ends of the sutures 1117 before welding the sutures together. The ends of the sutures 1117 were trimmed.

Figure 5L:
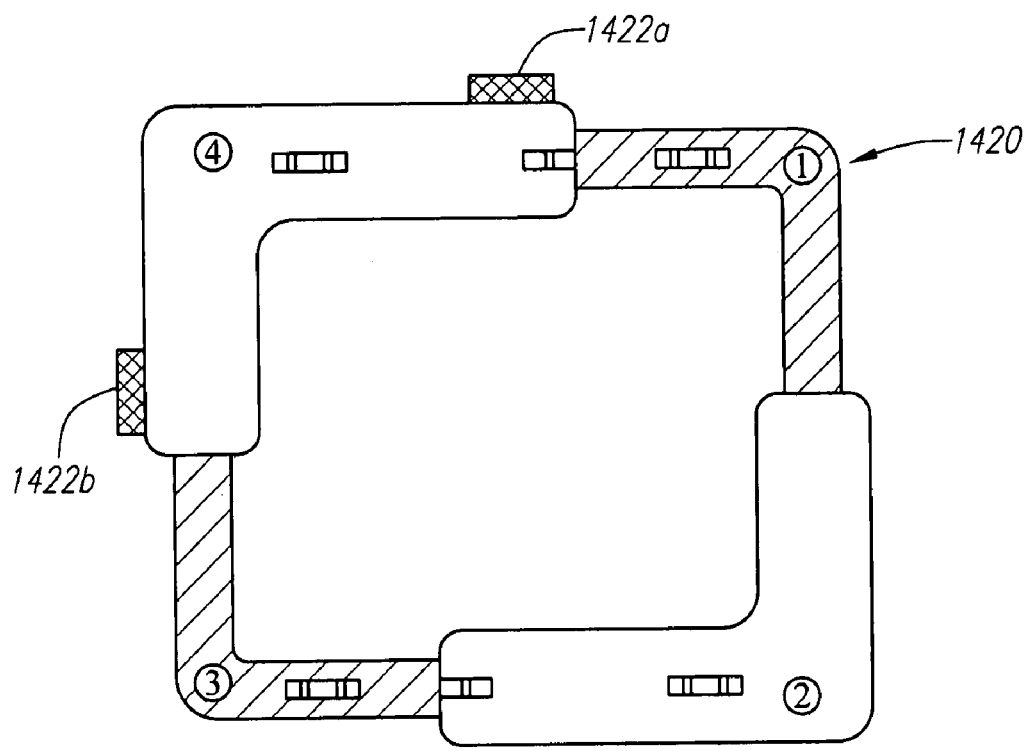
FIG. 5L is a posterior view of an alternative embodiment of a suture holding tool having components that telescope within each other.

FIG. 5L is a posterior view of an alternative embodiment of the suture holding tool drawn in FIG. 5D. The length and width of the tool may be adjusted by components that telescope within each other. Screws 1422*a, b* may be tightened to maintain the size of tool 1420. Slots for sutures are located in the top and bottom of the tool. The corners of the tool have numbers to help identify the sutures within the slots and the origin of the sutures. The tool is preferably between 8 and 20 cm in length and between 8 and 20 cm in width.

Figure 6A:
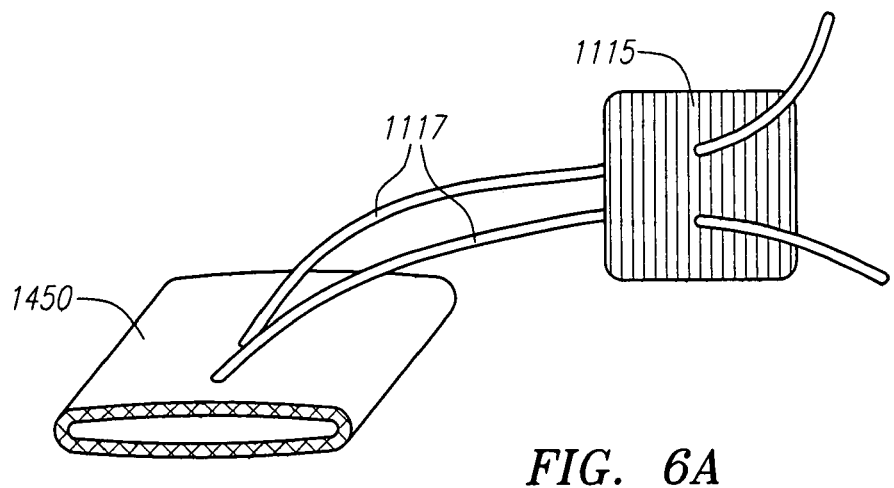
FIG. 6A. illustrates a mesh component having a tubular shape with an associated anti-adhesion component.

FIG. 6A is an alternative embodiment of the invention drawn in FIG. 5C. Mesh component 1450 has a tube shape. Alternatively, the mesh component may have two or more layers fastened together. The layers of mesh could be oriented perpendicular to one another in a bias-ply type of arrangement. The device also includes connecting suture 1117 and cover component 1115.

Figure 6B:
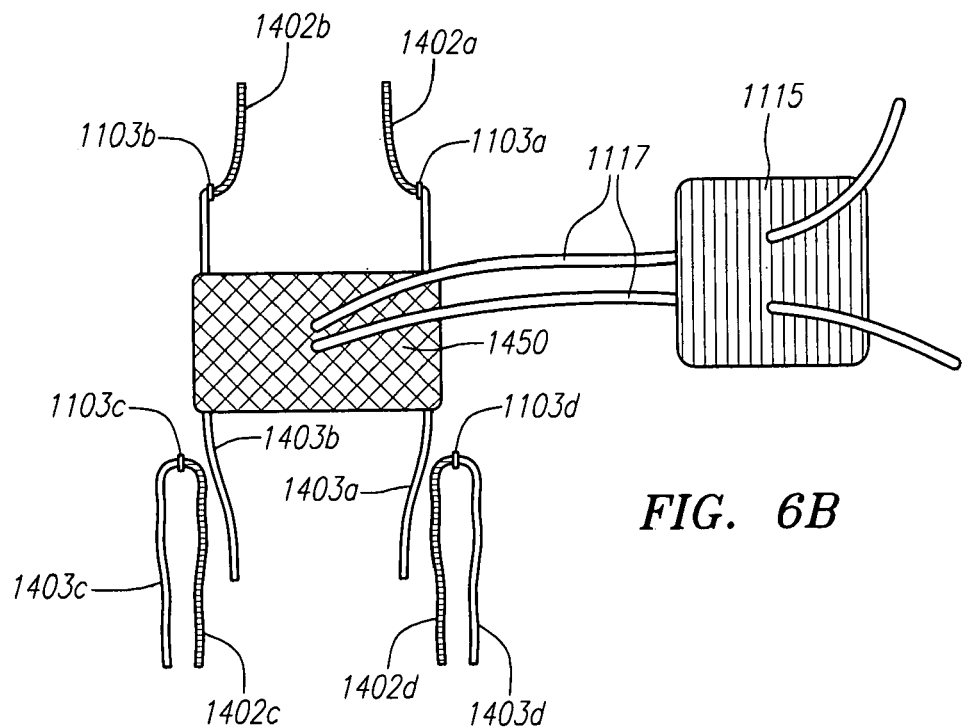
FIG. 6B is a posterior view of the embodiment of the invention drawn in FIG. 6A with the lateral ends of the sutures from the cranial pair of anchors passed between the layers of mesh.

FIG. 6B is a posterior view of the embodiment of the invention drawn in FIG. 6A. The lateral ends of the sutures 1403*a,b* from the cranial pair of anchors were passed between the layers of mesh 1450.

Figure 6C:
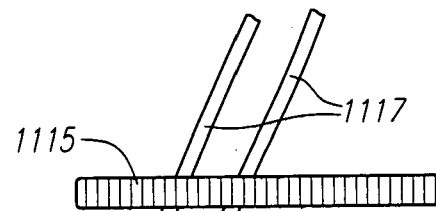
FIG. 6C is a lateral view of the embodiment of the invention drawn in FIG. 6B, which depicts lateral ends of sutures sandwiched between the layers of mesh and the connecting suture stitched through both layers of the mesh device.
Figure 6C:
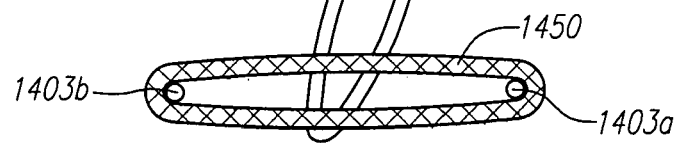

FIG. 6C is a lateral, view of the embodiment of the invention drawn in FIG. 6B, which depicts lateral ends 1403*a, b* of sutures sandwiched between the layers of mesh of device 1450. Connecting suture 1117 is stitched through both layers of mesh device 1450. Connecting suture 1117 is also threaded through anti-adhesion cover 1115.

Figure 6D:
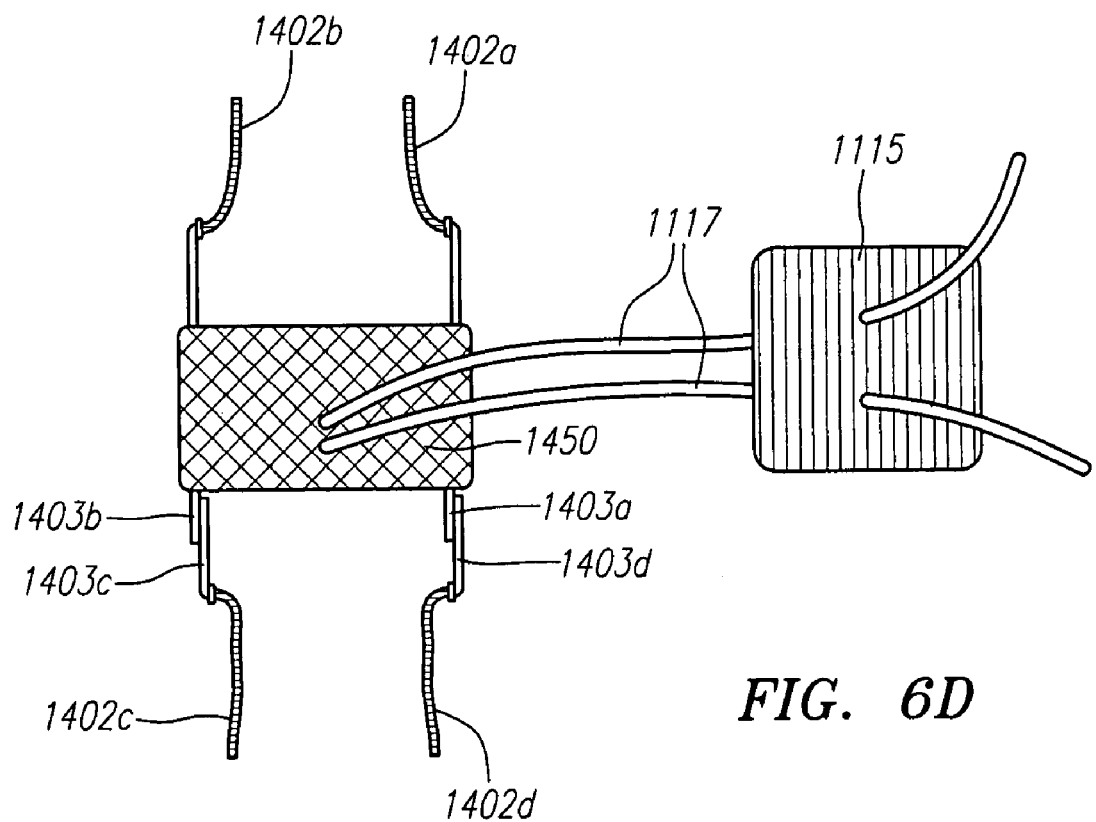
FIG. 6D is a posterior view of the embodiment of the invention drawn in FIG. 6B with the lateral ends of the sutures from the caudal pair of anchors welded to the lateral ends of the sutures from the cranial pair of anchors.

FIG. 6D is a posterior view of the embodiment of the invention drawn in FIG. 6B. The lateral ends of the sutures 1403*c, d* from the caudal pair of anchors were welded to the lateral ends of the sutures from the cranial pair of anchors 1403*a, b*. The weld can be performed outside the surgical wound.

Figure 6E:
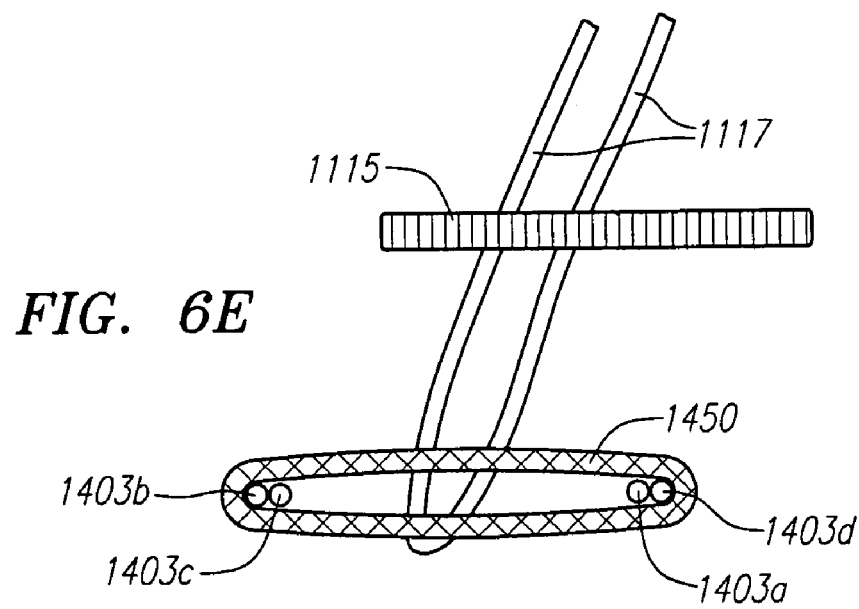
FIG. 6E is a lateral view of the embodiment of the invention drawn in FIG. 6D, which depicts lateral ends of sutures sandwiched between the layers of mesh of the device.

FIG. 6E is a lateral view of the embodiment of the invention drawn in FIG. 6D, which depicts lateral ends 1403*a-d* of sutures sandwiched between the layers of mesh of device 1450. Connecting suture 1117 is stitched through both layers of mesh device 1450. Connecting suture 1117 is also threaded through anti-adhesion cover 1115.

Figure 6F:
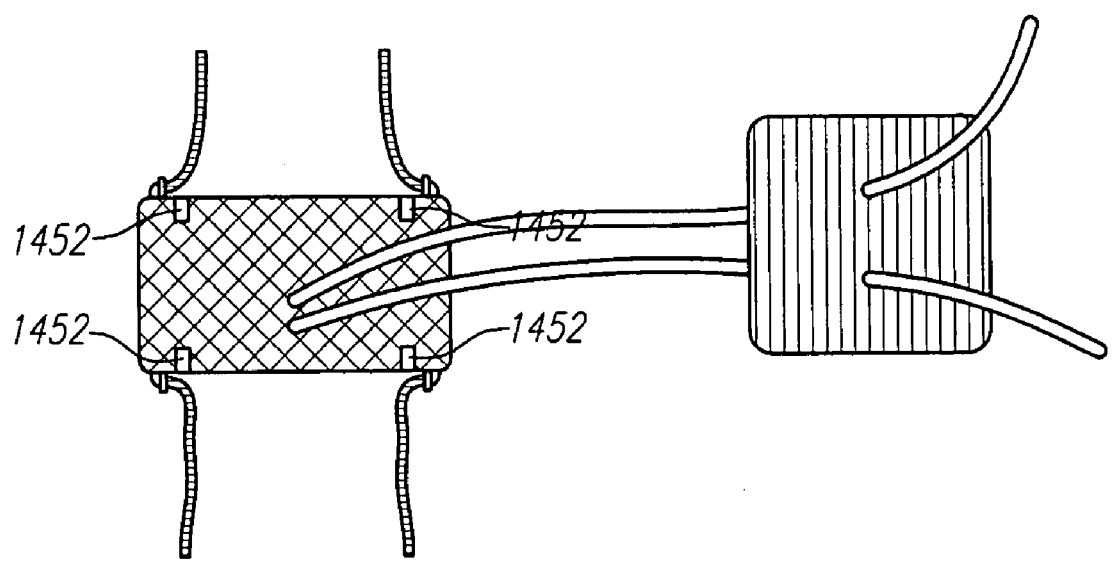
FIG. 6F is a posterior view of the embodiment of the invention drawn in FIG. 6D with the mesh layers "spot welded" just medial to the vertical arms of the fixation suture.

FIG. 6F is a posterior view of the embodiment of the invention drawn in FIG. 6D. The mesh layers were "spot welded" 1452 just medial to the vertical arms of the fixation suture (4 rectangular spotted areas). Welding the layers of mesh traps the vertical arms of the fixation suture within the mesh component. The "spot welds" 1452 can be performed outside the surgical wound. Tension was applied to the free ends of the vertical fixation sutures. Tension pulls the mesh patch into the wound and places the device over the disc.

Figure 6G:
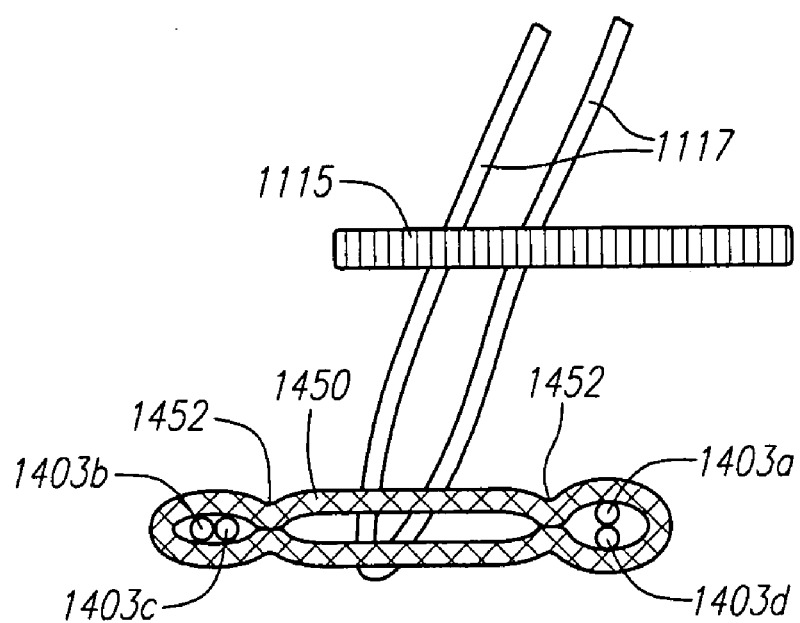
FIG. 6G is a lateral view of the embodiment of the invention drawn in FIG. 6F, which depicts lateral ends of sutures sandwiched between the layers of mesh of device.

FIG. 6G is a lateral view of the embodiment of the invention drawn in FIG. 6F, which depicts lateral ends 1403*a-d* of sutures sandwiched between the layers of mesh of device 1450. The "spot welds" 1452 are located just medial to the vertical arms of the fixation suture 1403. Connecting suture 1117 is stitched through both layers of mesh device 1450. Connecting suture 1117 is also threaded through anti-adhesion cover 1115.

Figure 6H:
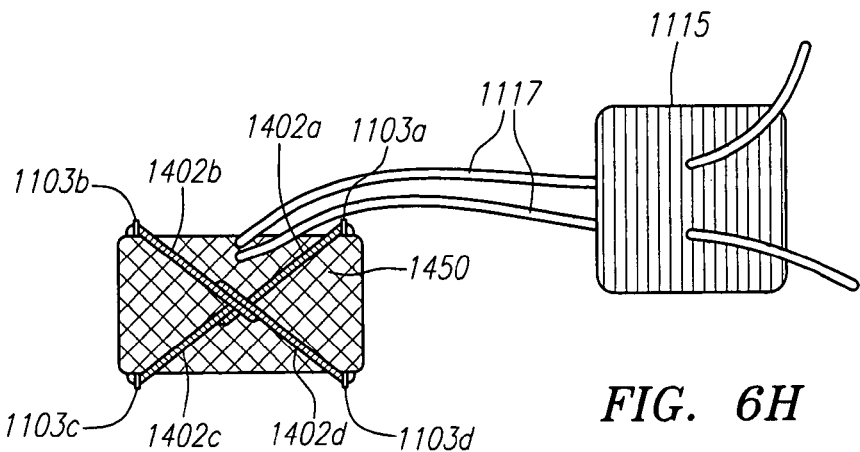
FIG. 6H is a posterior view of the embodiment of the invention drawn in FIG. 6G with the medial ends of the fixation sutures welded together.

FIG. 6H is a posterior view of the embodiment of the invention drawn in FIG. 6G. The medial ends of the fixation sutures were welded together in the manner described in the text of FIGS. 5G and 5H. The medial end of the fixation suture from the "10 o'clock" anchor 1402b was welded or otherwise fastened to the medial end of the suture from the "4 o'clock" anchor 1402d. Similarly, the medial ends of the "2 o'clock" 402a and the "8 o'clock" 402c fixation sutures were welded in the manner described in the text of FIG. 5G. Connecting suture 1117 does not surround the diagonal fixation sutures. This configuration reduces the profile of the assembled device.

Figure 6I:
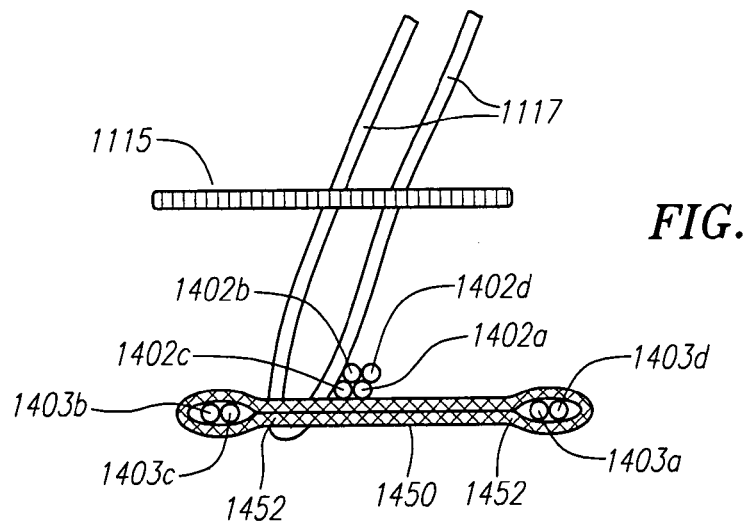
FIG. 6I is a lateral view of the embodiment of the invention drawn in FIG. 6H, which depicts the lateral ends of sutures sandwiched between the layers of mesh of the device.

FIG. 6I is a lateral view of the embodiment of the invention drawn in FIG. 6H, which depicts lateral ends 1403a-d of sutures sandwiched between the layers of mesh of device 1450. The "spot welds" 1452 are located just medial to the vertical arms of the fixation suture 1403. The cross-section of the medial ends of fixation sutures 1402a-d is shown on top of mesh device 1450. Connecting suture 1117 is stitched through both layers of mesh device 1450 and does not surround the diagonal fixation sutures. Connecting suture 1117 is also threaded through anti-adhesion cover 1115.

Figure 6J:
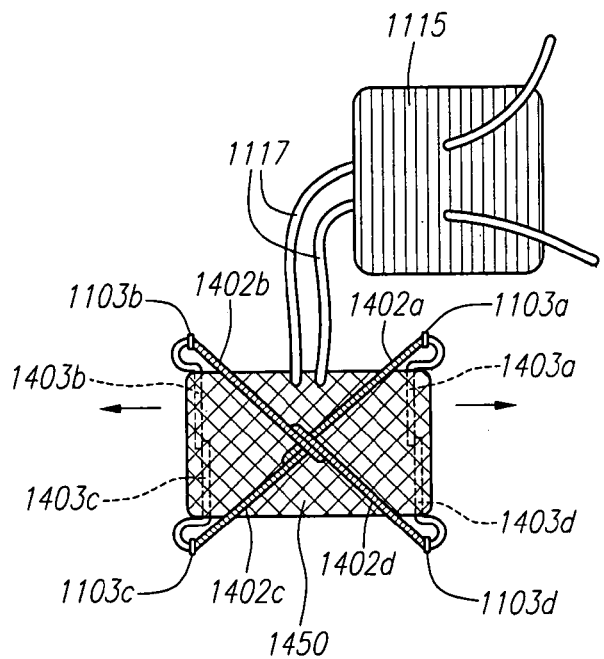
FIG. 6J is a posterior view of an alternative embodiment of the invention drawn in FIG. 6H.

FIG. 6J is a posterior view of an alternative embodiment of the invention drawn in FIG. 6H. The mesh component is narrower than the distance between the cranial and/or caudal pair of anchors 1103. Tension on the fixation sutures applies tension to the mesh component 1450. Tension on the mesh component 1450 increases the stiffness of the component.

Figure 7A:
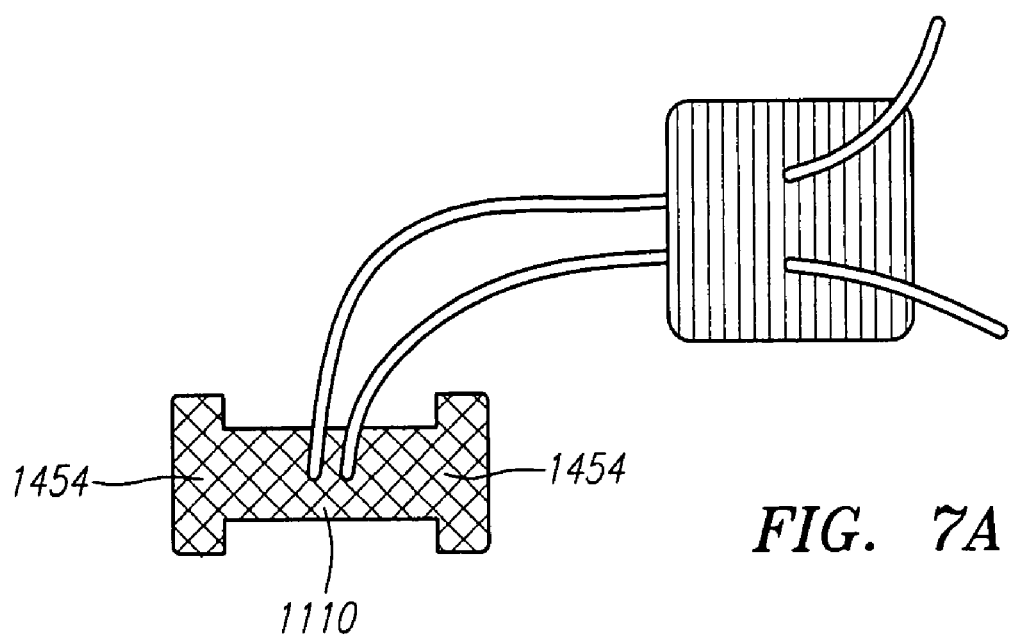
FIG. 7A is a posterior view of a mesh device having enlarged ends.

FIG. 7A is a posterior view of the embodiment of the invention drawn in FIG. 5C. The ends 1454 of the mesh component 1110 are enlarged.

Figure 7B:
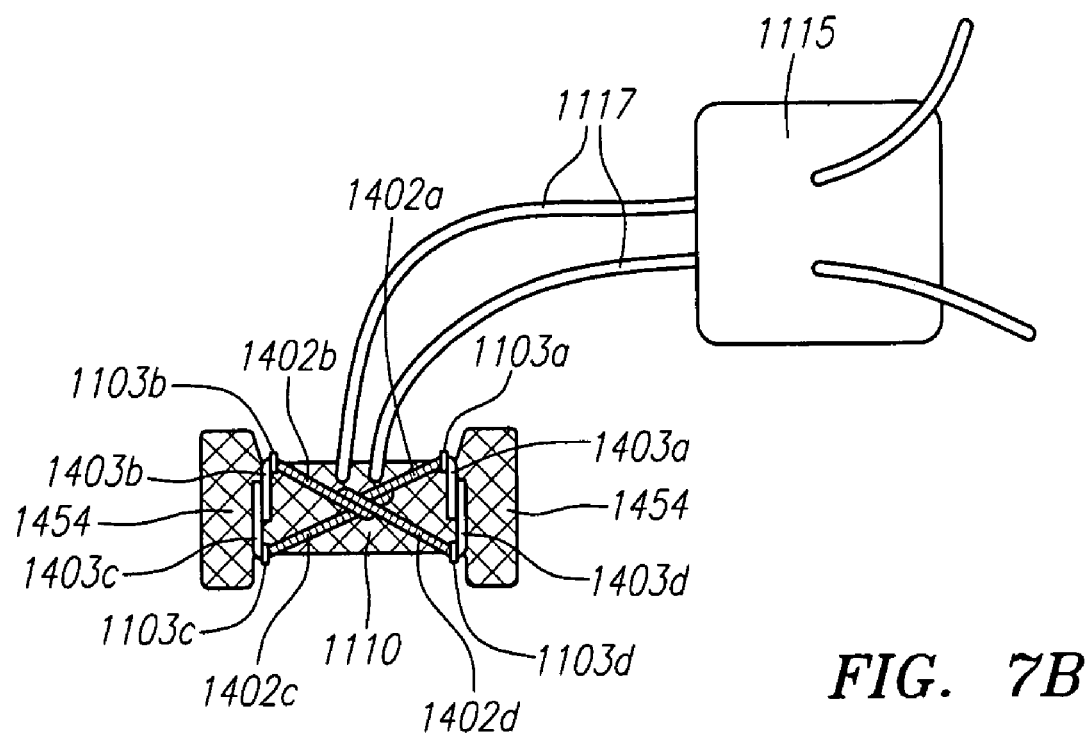
FIG. 7B is a posterior view of a mesh device where the enlarged ends extend beyond the cranial and the caudal pair of anchors.

FIG. 7B is a posterior view of the embodiments of the invention drawn in FIGS. 5J and 5A. The ends 1450 of the mesh 1110 extend beyond the cranial and the caudal pair of anchors 1103a-d. The configuration helps prevent the lateral edges of the mesh from migrating from under the vertical arms 1403a-d of the fixation sutures. The lateral edges of the mesh could contain a stiffening component to further reduce the risk of the edges migrating from under the vertical arms 1403a-d of the fixation sutures.

Figure 8A:
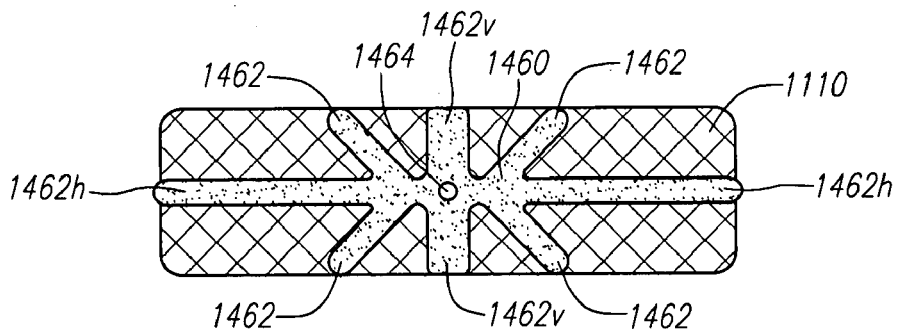
FIG. 8A is a posterior view of a weldable fixation component (star shaped) fastened to the mesh component.

FIG. 8A is posterior view of an alternative embodiment of the invention drawn in FIG. 5C. A weldable fixation component (star shaped) 1460 has been fastened to the mesh component 1110. The weldable fixation component 1460 may have a plurality of extensions 1462 that substantially extend to the edges of mesh component 1110. The extensions may include two horizontal arms 1462h, two vertical arms 1462v, and four diagonal arms 1462. The weldable fixation component 1460 is preferably stiffer than the mesh component 1110. The weldable fixation component 1460 is preferably made of nylon or polyester and can be about 0.5 mm thick. Alternatively, the weldable fixation component 1460 can be made of materials other than nylon or polyester and may be between 0.1 and 3.0 mm thick. The weldable fixation component 1460 may have features that enable attachment of the cover component. For example, the weldable fixation component 1460 may have a hole 1464 that receives a projection from the cover component. The fixation component 1460 is preferably stiffer than the mesh.

Figure 8B:
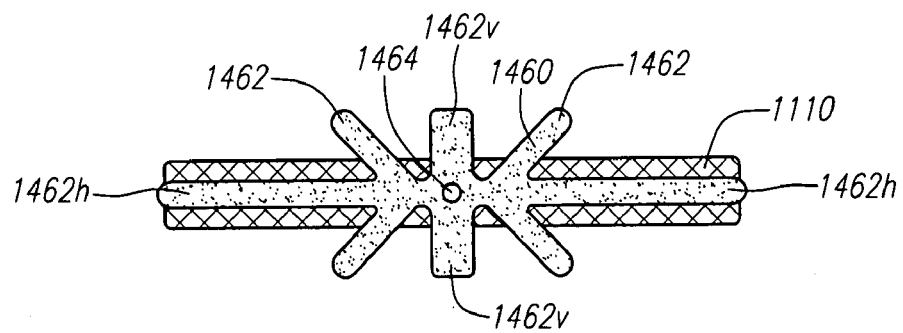
FIG. 8B is a posterior view a weldable fixation component where mesh is fastened to only a portion of the fixation component.

FIG. 8B is a posterior view of the embodiment of the invention drawn in FIG. 8A. The mesh 1110 is preferably fastened to only a portion of the fixation component 1460. For example, the mesh 1110 may be fastened to the horizontal arms 462h of the fixation component.

Figure 8C:
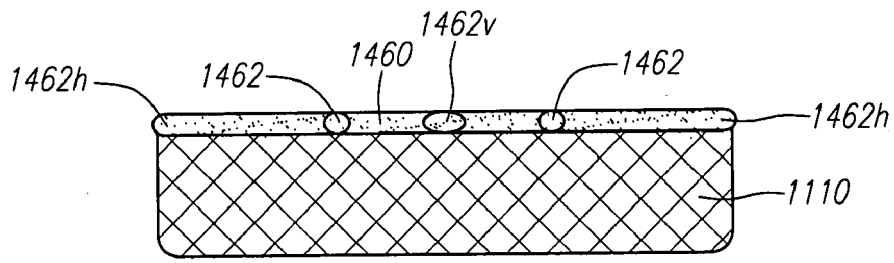
FIG. 8C is a lateral view of the embodiment of the invention drawn in FIG. 8B.

FIG. 8C is a lateral view of the embodiment of the invention drawn in FIG. 8B. This illustrates that the mesh component 1110 is attached to the horizontal extensions 1462h.

Figure 8D:
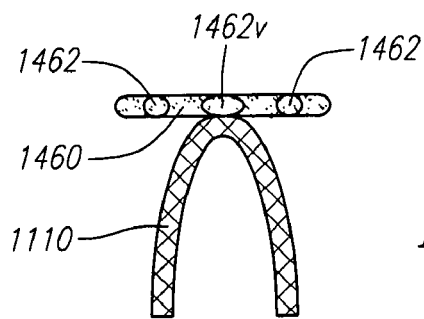
FIG. 8D is an end view of the embodiment of the invention drawn in FIG. 8C.

FIG. 8D is an end view of the embodiment of the invention drawn in FIG. 8C, which also illustrates that the mesh component 1110 is attached to the horizontal extensions 1462h.

Figure 8E:
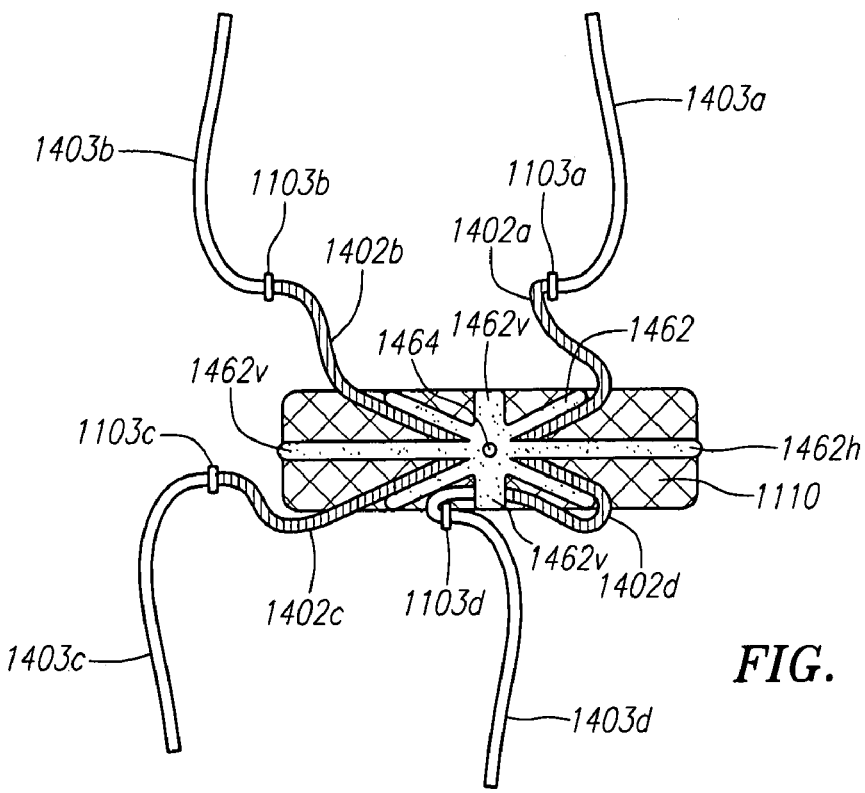
FIG. 8E is a posterior view a weldable fixation component attached to a mesh patch where the sutures were welded to the diagonal arms of the fixation component.

FIG. 8E is a posterior view of the embodiments of the invention drawn in FIGS. 5A and 8A. The medial ends of the fixation sutures 1402a-d were welded to the diagonal arms 1462 of the fixation component 1460. The welds are preferably performed outside the surgical wound.

Figure 8F:
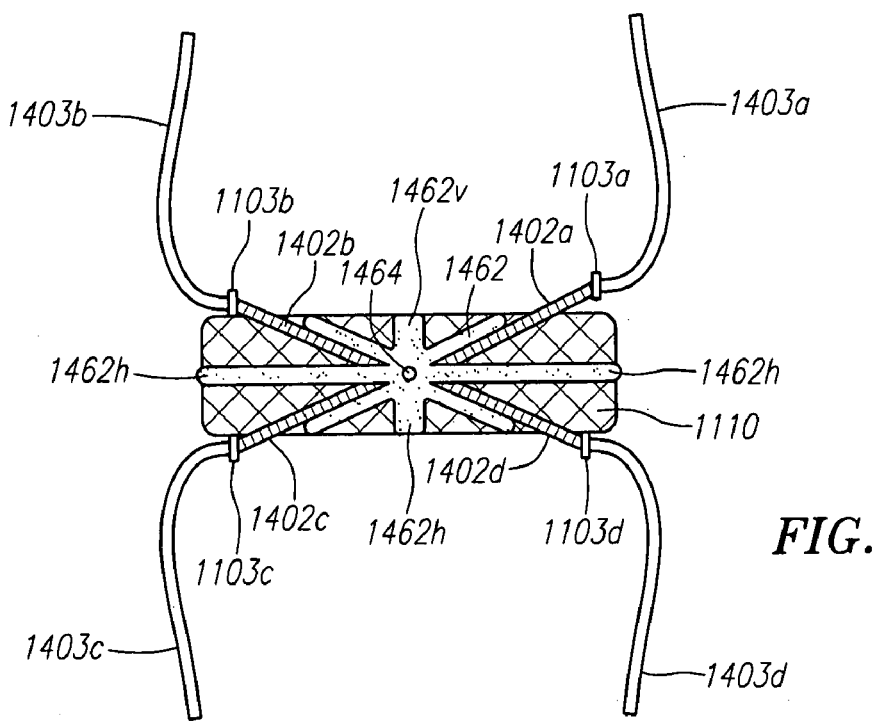
FIG. 8F is a posterior view of the embodiment of the invention drawn in FIG. 8E.

FIG. 8F is a posterior view of the embodiment of the invention drawn in FIG. 8E. Tension was applied to the free ends of the fixation suture 1403a-d to pull the mesh component 1110 into the wound and place the mesh component 1110 over the disc (not shown).

Figure 8G:
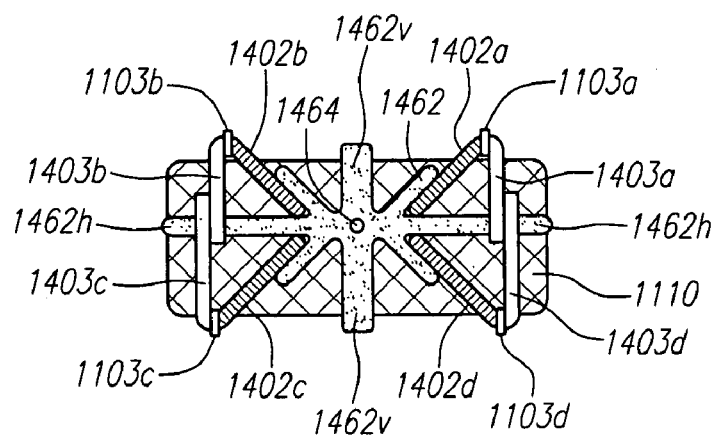
FIG. 8G is a posterior view of the embodiment of the invention drawn in FIG. 8F with the lateral ends of the fixation sutures welded together.

FIG. 8G is a posterior view of the embodiment of the invention drawn in FIG. 8F. The lateral ends 1403a-d of the fixation sutures were welded together in the manner described in the text of FIG. 5I. The lateral end of the "2 o'clock" suture 4103a was welded to the lateral end of the "4 o'clock" suture 1403d. The lateral end of the "8 o'clock" suture 1403c was welded to the lateral end of the "10 o'clock" suture 1403b. Tension was applied to the ends of the sutures before welding the sutures. Tension on the final two pair of welded sutures, before welding the sutures, tightens all the welded fixation sutures. The ends of the sutures are preferably cut with guillotine-like arthroscopic suture cutter. The vertical fixation arms 1403a-d preferably lie over the horizontal arms 1462h of the fixation device.

Figure 8H:
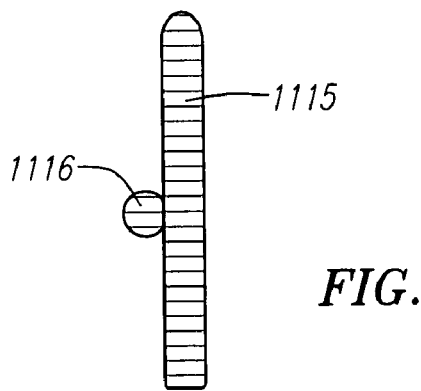
FIG. 8H is a lateral view of an alternative embodiment of an anti-adhesion cover.

FIG. 8H is a lateral view of an alternative embodiment of cover component 1115. The distal portion of the cover 1115 has a projection 1116. The projection 1116 from the cover 1115 can be snapped into the hole 1464 of the fixation component 1460. Alternative methods may be used to connect the two components.

Figure 8I:
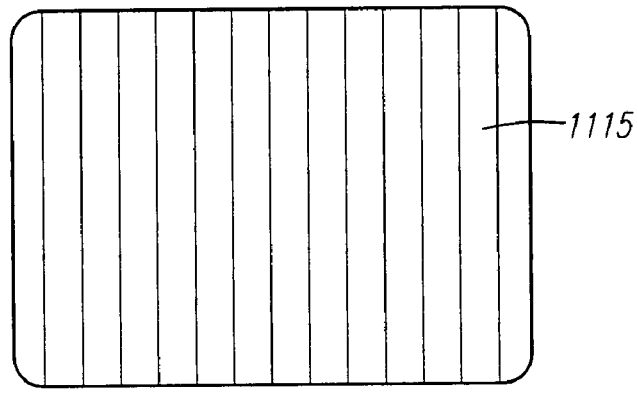
FIG. 8I is a posterior view of the embodiments of the invention drawn in FIGS. 8G and 8H.

FIG. 8I is a posterior view of the embodiments of the invention drawn in FIGS. 8G and 8H. The cover component 1115 has been fastened to the mesh or fixation components (not shown).

Figure 9A:
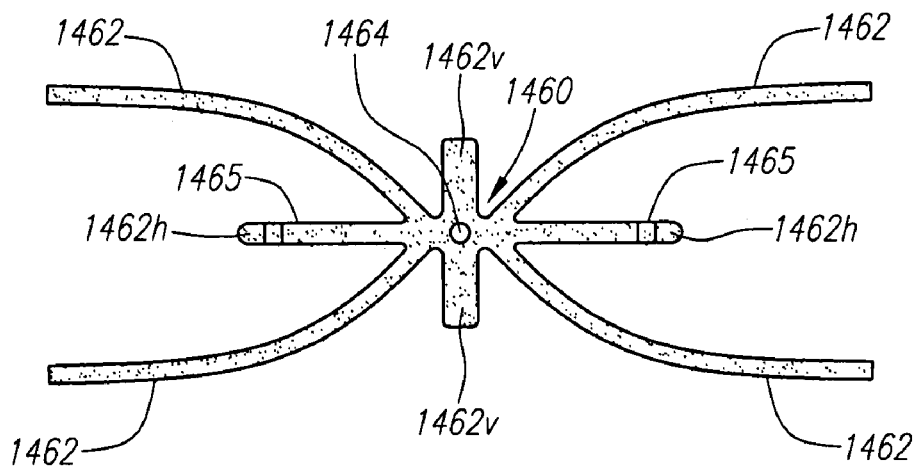
FIG. 9A is a posterior view of an alternative embodiment a weldable fixation component with long diagonal arms.

FIG. 9A is a posterior view of an alternative embodiment of the invention drawn in FIG. 8A. The fixation component has long diagonal arms 1462. The ends of the horizontal arms 1462h of the fixation component have recessed regions (small vertical rectangles) 1465. The long arms 1462 facilitate use of the welding tool. The excess suture is cut after welding the sutures together. The excess suture was removed in FIGS. 9B-9D.

Figure 9B:
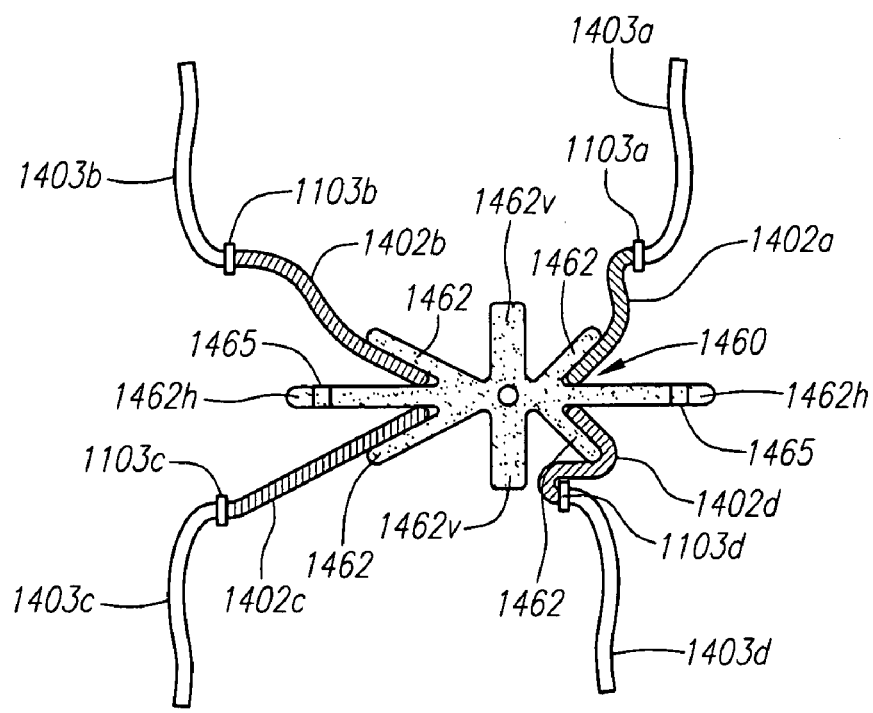
FIG. 9B is a posterior view of the embodiments of the invention drawn in FIGS. 5A and 9A.

FIG. 9B is a posterior view of the embodiments of the invention drawn in FIGS. 5A and 9A. The medial ends 1402a-d of the fixation sutures were welded, or otherwise connected, to the diagonal arms 1462 of the fixation component 1460. The ends of the welded sutures were cut and removed.

Figure 9C:
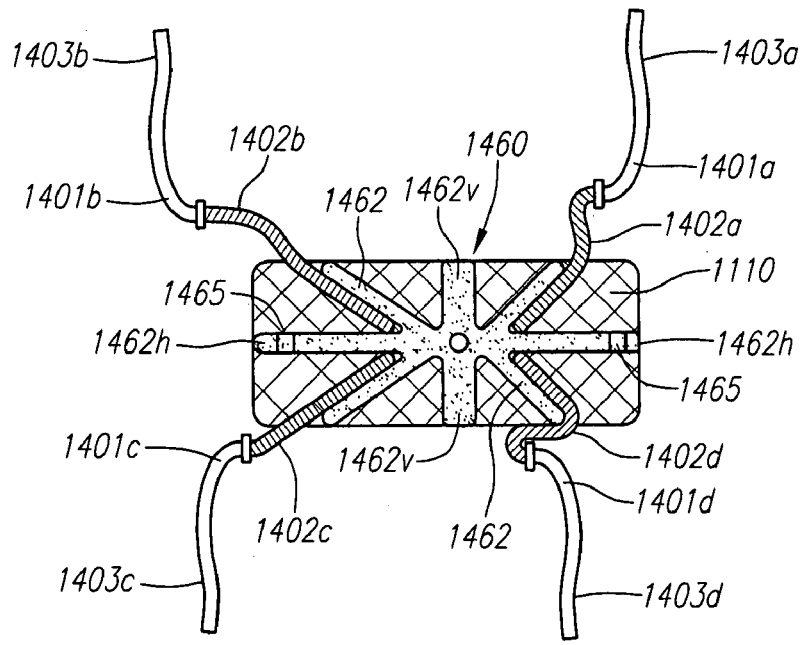
FIG. 9C is a posterior view of the embodiment of the invention drawn in FIG. 9B.

FIG. 9C is a posterior view of the embodiment of the invention drawn in FIG. 9B. The fixation component 1460 with the welded fixation sutures 1401a-d was fastened to a mesh component 1110. The components can be welded together. Other fastening methods or devices may be used to connect the two components. The two components are preferably fastened together outside the wound. Tension is applied to the free ends of the fixation sutures 1401a-d to pull the assembled device into the wound and place the device over the disc.

Figure 9D:
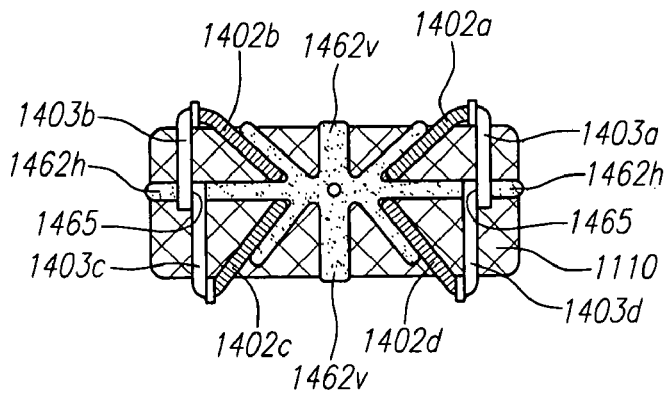
FIG. 9D is a posterior view of the embodiment of the invention drawn in FIG. 9C, which shows the vertical arms of the fixation sutures welded together.

FIG. 9D is a posterior view of the embodiment of the invention drawn in FIG. 9C. The vertical arms of the fixation sutures 1403a-d were welded together in the manner described in the text of FIG. 5I. The welded vertical fixation sutures preferably sit within the recessed portions 1465 of the horizontal arms 1462*h* of the fixation component 460.

Figure 9E:
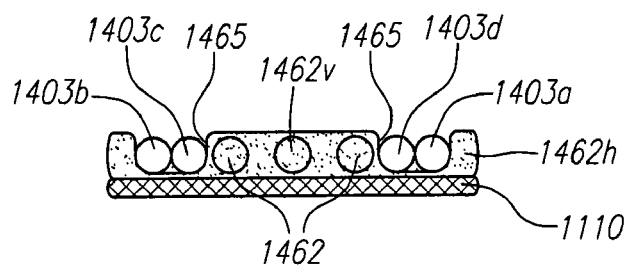
FIG. 9E is a lateral view of the embodiment of the invention drawn in FIG. 9D, which illustrates the vertical arms sitting within recessed regions of the horizontal arms.

FIG. 9E is a lateral view of the embodiment of the invention drawn in FIG. 9D, which illustrates the vertical arms (or lateral sutures) 1403*a-d* sitting within recessed regions 1465 of the horizontal arms 1462*h*.

Figure 10A:
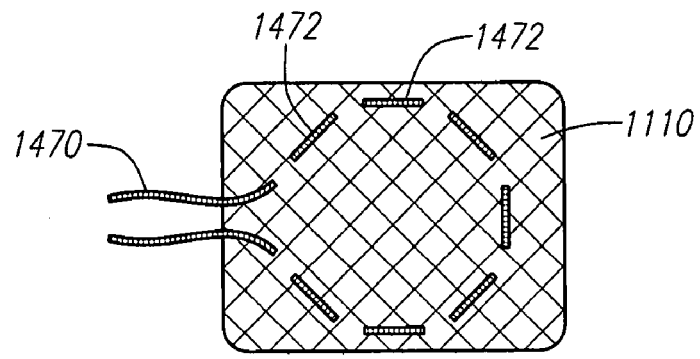
FIG. 10A is a posterior view of a mesh patch with a weldable suture threaded therethrough.

FIG. 10A is a posterior view of an alternative embodiment of the invention drawn. A weldable suture 1470 was threaded through the mesh component 1110 such that exposed stitches 1472 are visible on the top side of the mesh component 1110.

Figure 10B:
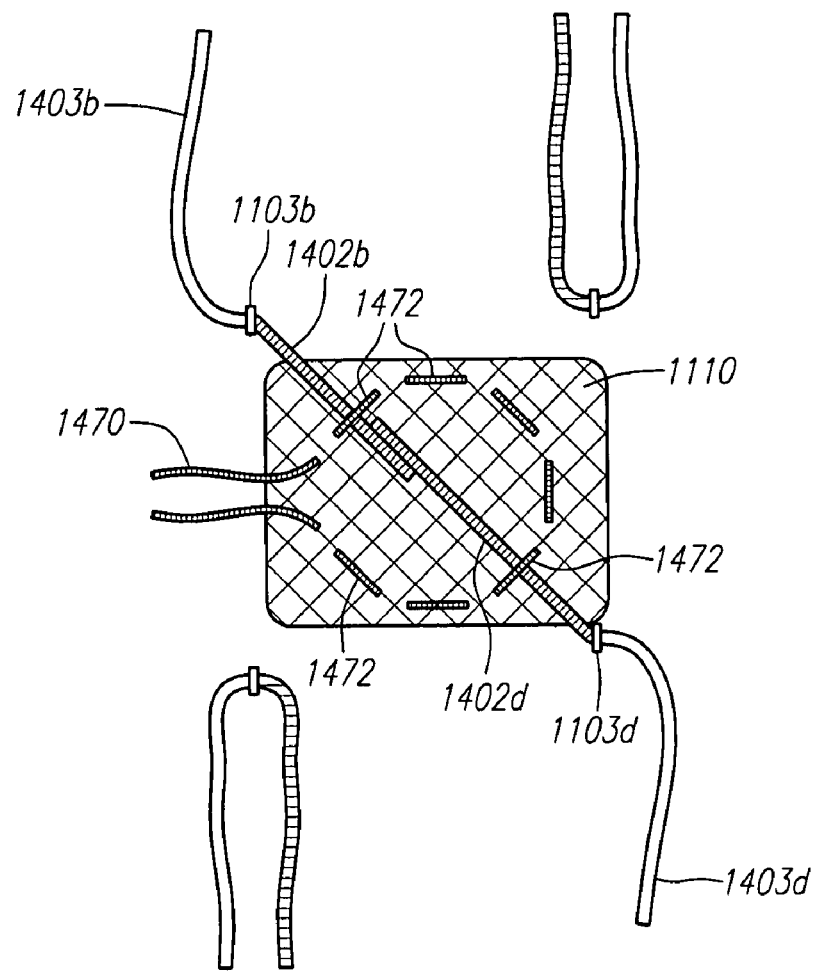
FIG. 10B is a posterior view of the embodiments of the invention drawn in FIG. 10A with two fixation sutures passed under "purse string" suture.

FIG. 10B is a posterior view of the embodiments of the invention drawn in FIG. 10A. The medial end 1402*b* of the "10 o'clock" suture was passed under the "purse string" suture or exposed stitch 1472 and welded to the medial end of the "4 o'clock" suture 1402*d* after passing that end under a second portion of the "purse string" or exposed stitch 1472.

Figure 10C:
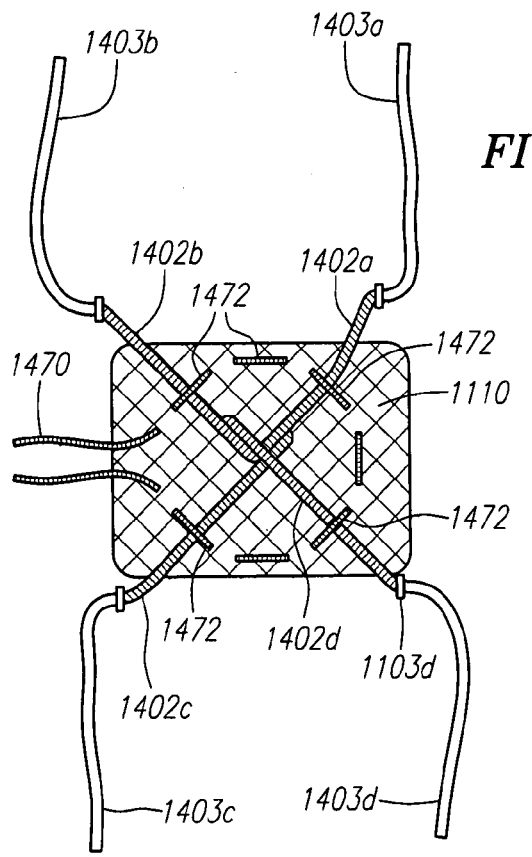
FIG. 10C is a posterior view of the embodiment of the invention drawn in FIG. 10B with two more sutures passed under the "purse string."

FIG. 10C is a posterior view of the embodiment of the invention drawn in FIG. 10B. The medial ends of the "2 o'clock" 1402*a* and "8 o'clock" 1402*c* sutures were passed under the "purse string" 1472 and welded together.

Figure 10D:
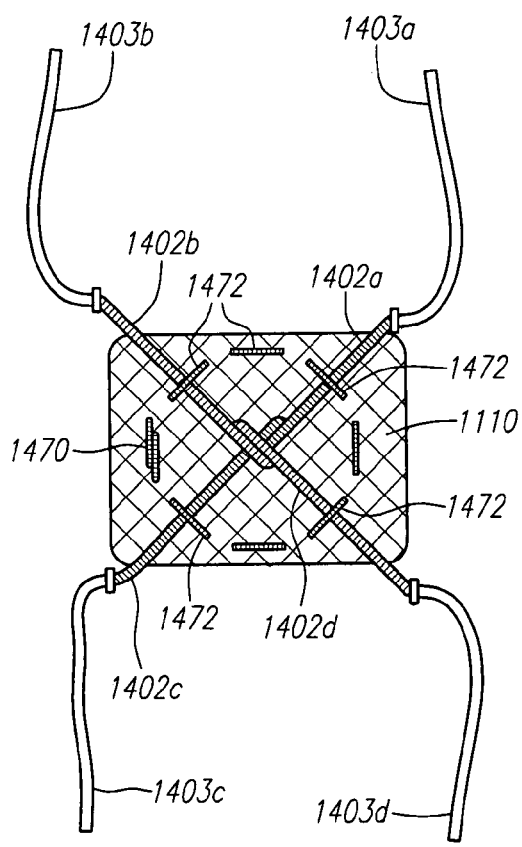
FIG. 10D is a posterior view of the embodiment of the invention drawn in FIG. 10C with the ends of the "purse string" welded together.

FIG. 10D is a posterior view of the embodiment of the invention drawn in FIG. 10C. The ends of the "purse string" 1470 were welded together after applying tension to the ends of the suture. The ends of the "purse string" are preferably welded together outside the wound. Tension is applied to the free ends of the fixation sutures 1403*a-d* to pull the assembled device into the wound and place the device over the disc (not shown).

Figure 10E:
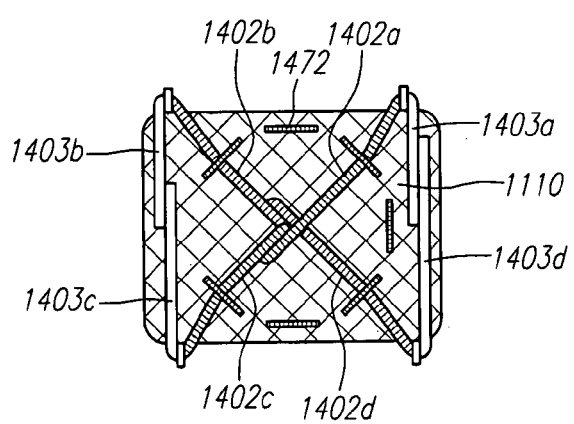
FIG. 10E is a posterior view of the embodiment of the invention drawn in FIG. 10D with the lateral ends of the fixation sutures welded together.

FIG. 10E is a posterior view of the embodiment of the invention drawn in FIG. 10D. The lateral ends of the fixation sutures 1403*a-d* were welded together in the manner described in the text of FIG. 5I. The lateral end of the "2 o'clock" suture 1403*a* was welded to the lateral end of the "4 o'clock" suture 1403*d*. The lateral end of the "8 o'clock" suture 1403*c* was welded to the lateral end of the "10 o'clock" suture 1403*b*. Tension was applied to the ends of the sutures before welding the sutures. Tension on the final two pair of welded sutures, before welding the sutures, tightens all the welded fixation sutures. The ends of the sutures are preferably cut with guillotine-like arthroscopic suture cutter. A cover component may be attached to the fixation sutures or the mesh component.

Figure 11:
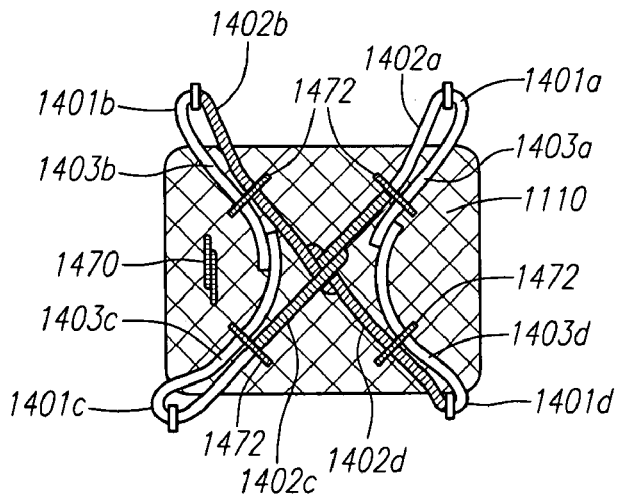
FIG. 11 is a posterior view of an alternative mesh component with a "purse string" or suture placed such that exposed stitches are positioned closer to the center of the mesh.

FIG. 11 is a posterior view of an alternative embodiment of the invention drawn in FIG. 10E. The "purse string" or suture 1470 is placed such that exposed stitches 1472 are positioned closer to the center of the mesh. This configuration enables the fixation sutures 1401*a-d* to apply tension to the mesh 1110. The fixation sutures apply tension in at least the cranial to caudal direction and the left to right direction.

Figure 12A:
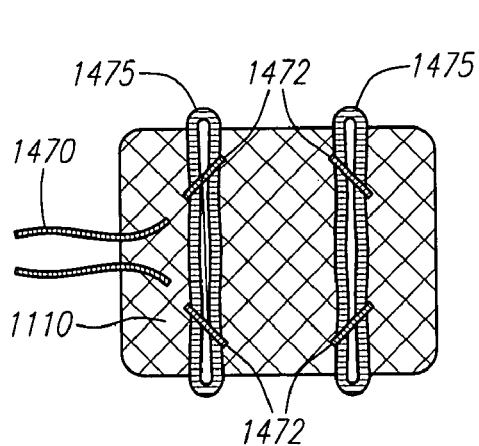
FIG. 12A is a posterior view of an alternative embodiment a mesh patch having two loops passed under a "purse string."

FIG. 12A is a posterior view of an alternative embodiment of the invention drawn in FIG. 10A. Two loops 1475 were passed under the "purse string" or exposed stitches 1472. The loops 1475 are preferably made of nylon or other somewhat stiff material.

Figure 12B:
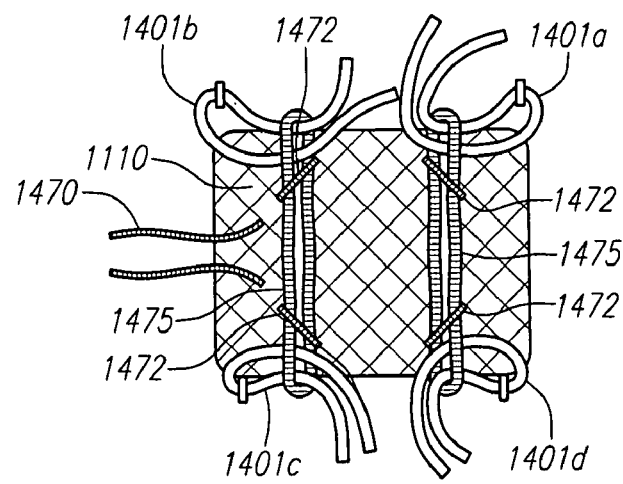
FIG. 12B is a posterior view of the alternative embodiment of FIGS. 5A where the ends of the fixation sutures were passed through the openings in the loops.

FIG. 12B is a posterior view of the embodiment's invention drawn in FIGS. 5A and 12A. The ends of the fixation sutures 1401*a-d* were passed through the openings in the loops 1475.

Figure 12C:
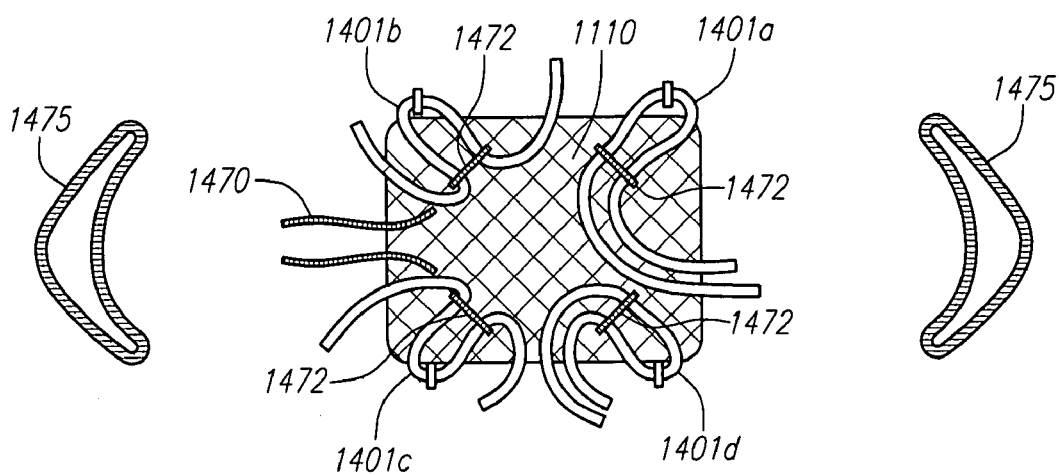
FIG. 12C is an exploded posterior view of the embodiment of the invention drawn in FIG. 12B.

FIG. 12C is an exploded posterior view of the embodiment of the invention drawn in FIG. 12B. The loops 1475 were removed from the mesh 1110. The loops were removed by pulling on the central portion of the loops. The ends of the fixation sutures 1401*a-d* were pulled under the purse string 1472 as the loops 1475 were removed from the mesh 1110. The purse string 1470 is tightened and welded in the manner taught in FIG. 10C. The fixation sutures 1401*a-d* may be welded in the manner described in the text of FIGS. 5G through 5I.

Figure 12D:
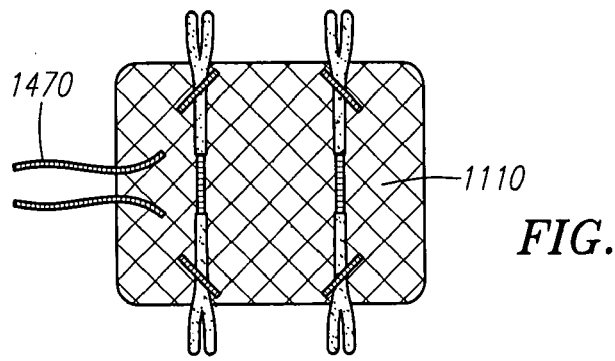
FIG. 12D is a posterior view of an alternative mesh patch where the 1475 of FIG. 12A were replaced by devices with slit-like ends.

FIG. 12D is a posterior view of an alternative embodiment of the invention drawn in FIG. 12A. Loops 1475 of FIG. 12A were replaced by devices with slit-like ends. The ends of the fixation sutures 1401*a-d* are press fit into the slots/slits at the ends of the components that were placed under the "purse string" 1470. The purse string 1470 is tightened and welded in the manner taught in FIG. 10C. The fixation sutures 1401*a-d* are welded together in the manner taught in FIGS. 5G to 5I.

Figure 13:
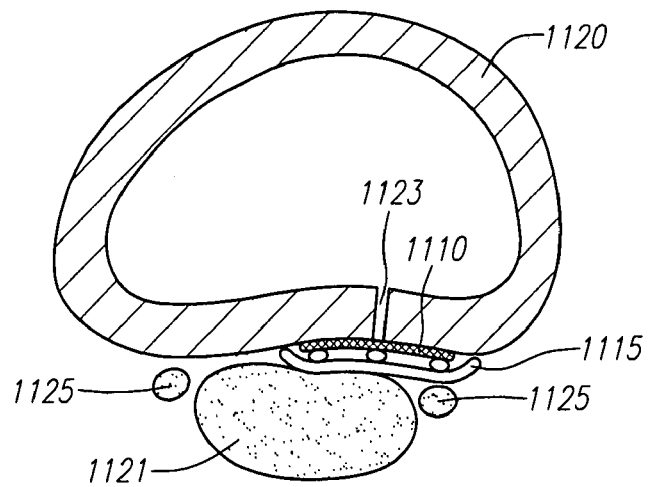
FIG. 13 is an axial cross section of a disc, the thecal sac, nerves, and the embodiment of the invention drawn in FIG. 5K.

FIG. 13 is an axial cross section of a disc 1120, the thecal sac 1121, nerves 1125, and the embodiment of the invention drawn in FIG. 5K. The device comprising a mesh component 1110, fixation and connecting sutures, and anti-adhesion cover 1115 was placed on the left side of the posterior aspect of the disc 1120. Eccentrically placed devices are used to treat defects of the disc that are limited to one side of the disc.

Figure 14:
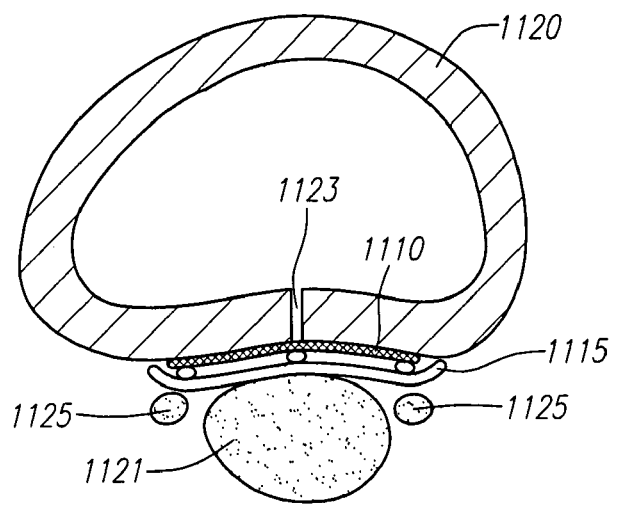
FIG. 14 is an axial cross section of a disc, the thecal sac, nerves, and the embodiment of the invention drawn in FIG. 5K, where the device is used to treat a defect across a central portion of the posterior aspect of the disc.

FIG. 14 is an axial cross section of a disc 1120, the thecal sac 1121, nerves 1125, and the embodiment of the invention drawn in FIG. 5K. The device comprising a mesh component 1110, fixation and connecting sutures, and anti-adhesion cover 1115 extends across most of the posterior aspect of the disc 1120. Such placed devices are used to treat defects 1123 across central portion of the posterior aspect of the disc 1120.

Figure 15A:
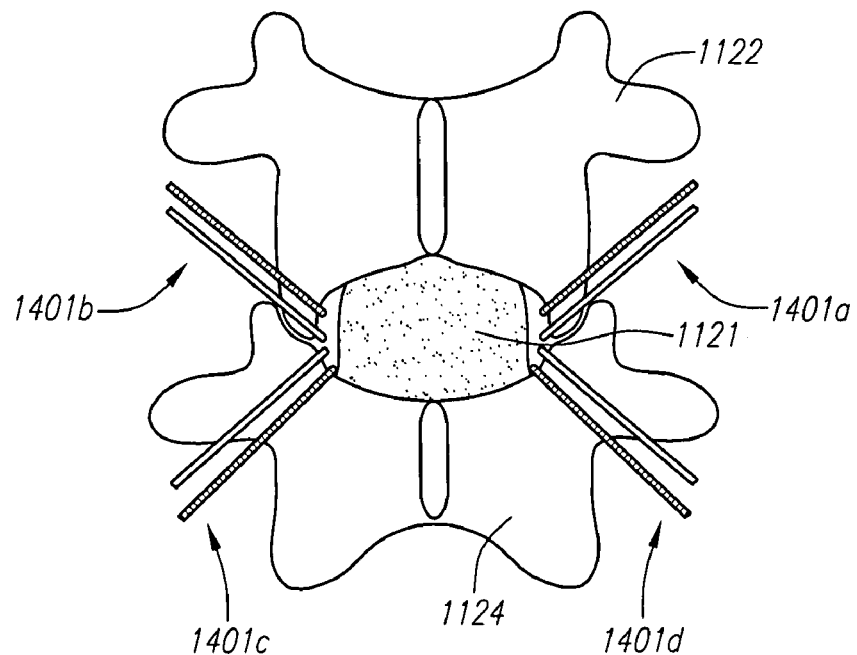
FIG. 15A is a posterior view of a portion of the spine where fixation sutures are seen exiting the spinal canal lateral to the thecal sac.

FIG. 15A is a posterior view of a portion of the spine and the embodiment of the invention drawn in FIG. 5A. Fixation sutures 1401*a-d* are seen exiting the spinal canal lateral to the thecal sac 1121. Anchors were placed in the left and the right sides of the posterior aspects of the vertebrae 1122, 1124.

Figure 15B:
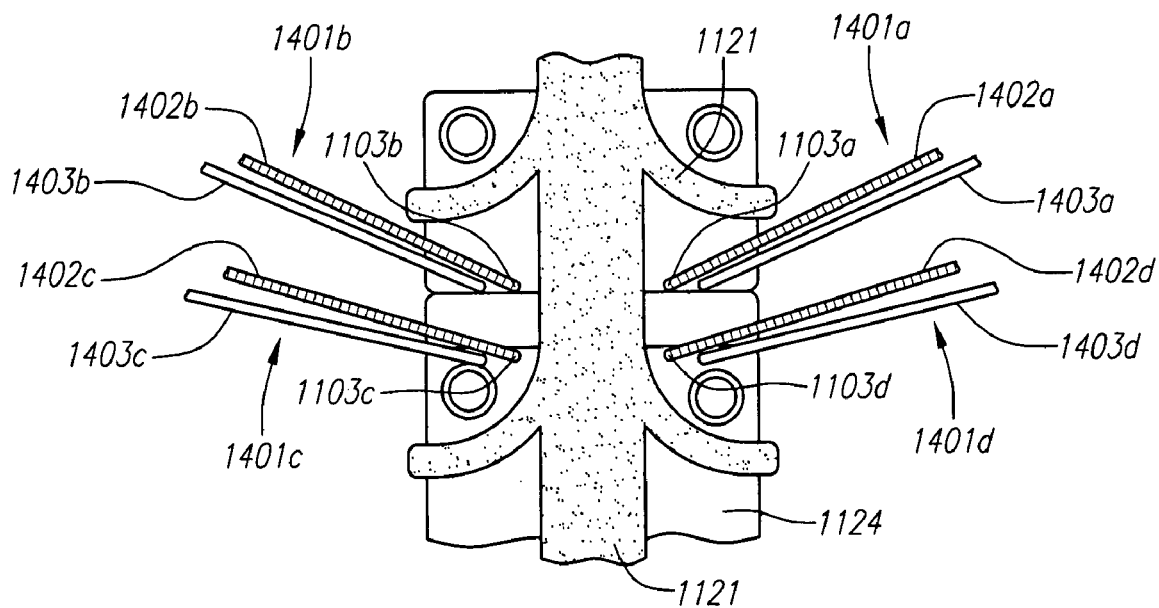
FIG. 15B is a posterior view of a coronal cross section of the spine and the embodiment of the invention drawn in FIG. 15A.

FIG. 15B is a posterior view of a coronal cross section of the spine and the embodiment of the invention drawn in FIG. 15A. The anchors 1103*a-d* and sutures 1401*a-d* are seen on the left and the right sides of the thecal sac 1121.

Figure 15C:
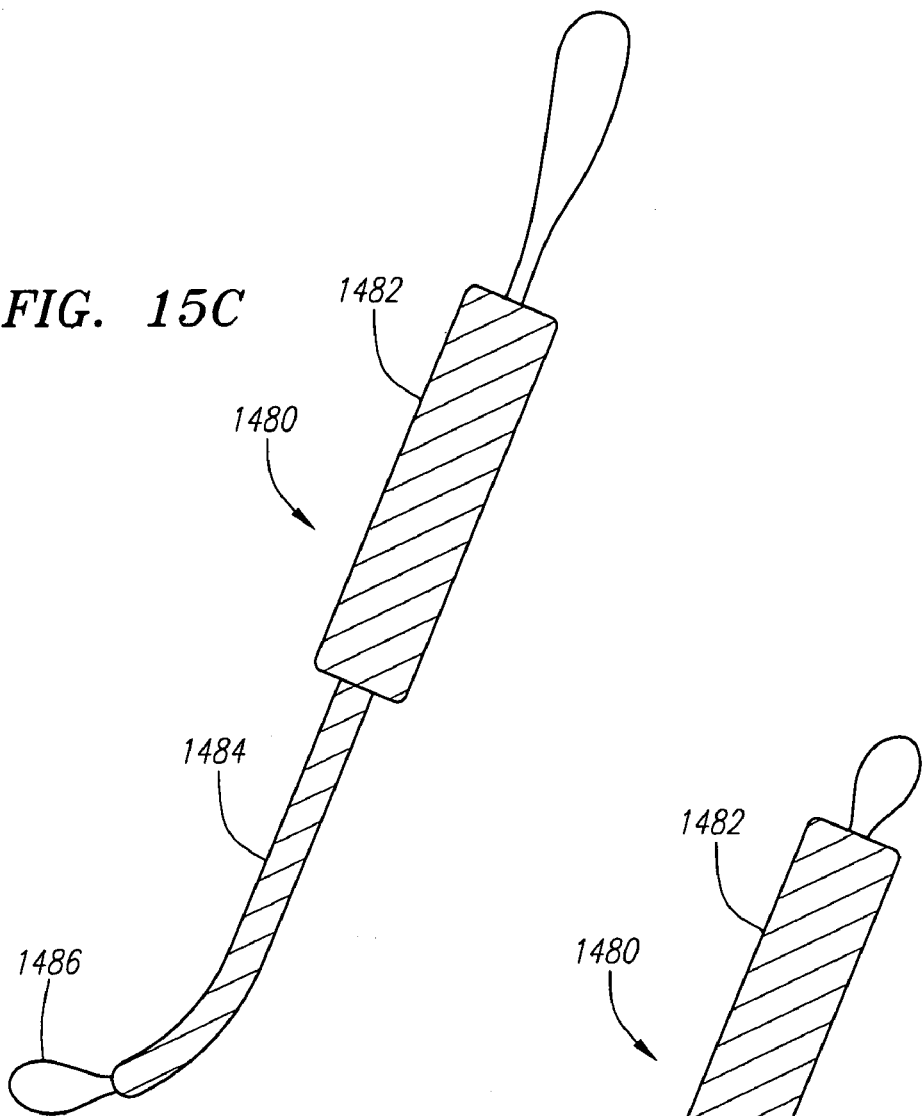
FIG. 15C is a lateral view of a suture passing tool.

FIG. 15C is a lateral view of a suture passing tool 1480. Suture passing tool 1480 has a handle 1482, flexible, curved distal portion 1484 with a loop 1486 passing through a lumen of the curved distal portion 1484.

Figure 15D:
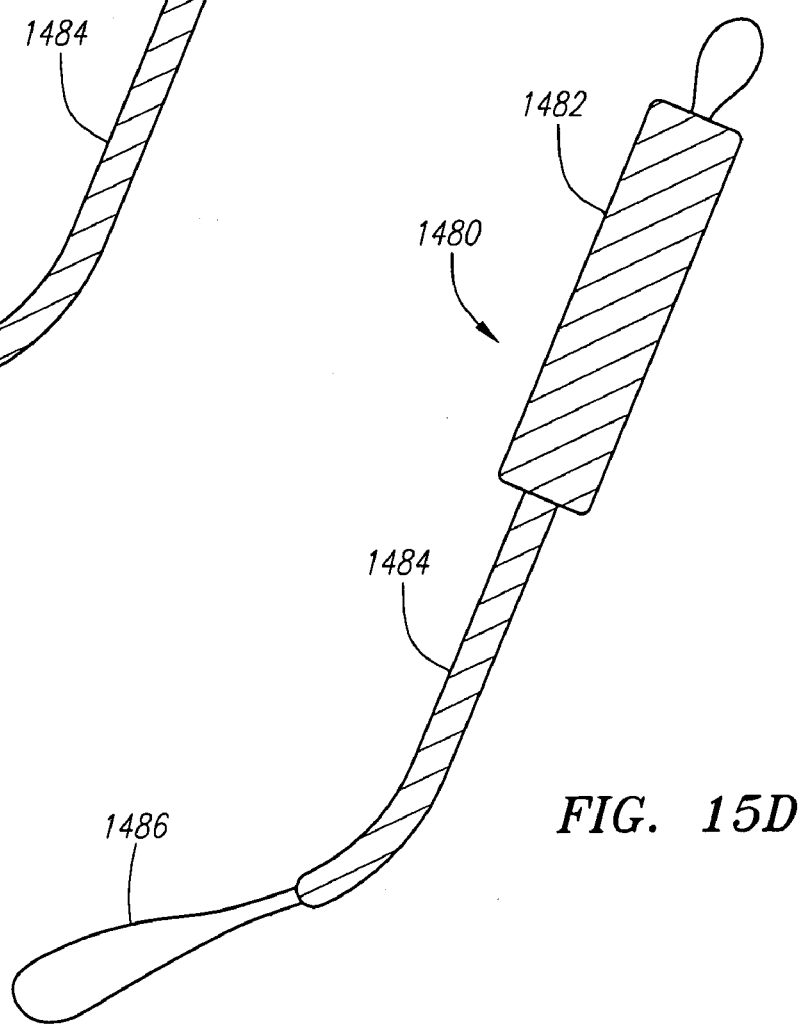
FIG. 15D is a lateral view of the suture tool drawn in FIG. 15C with the loop that passes through the tool advanced further out the distal end of the tool.

FIG. 15D is a lateral view of the suture tool drawn 1480 in FIG. 15C. The loop 1486 that passes through the tool has been advanced further out the distal end of the tool 1480 than the loop drawn in FIG. 15C.

Figure 15E:
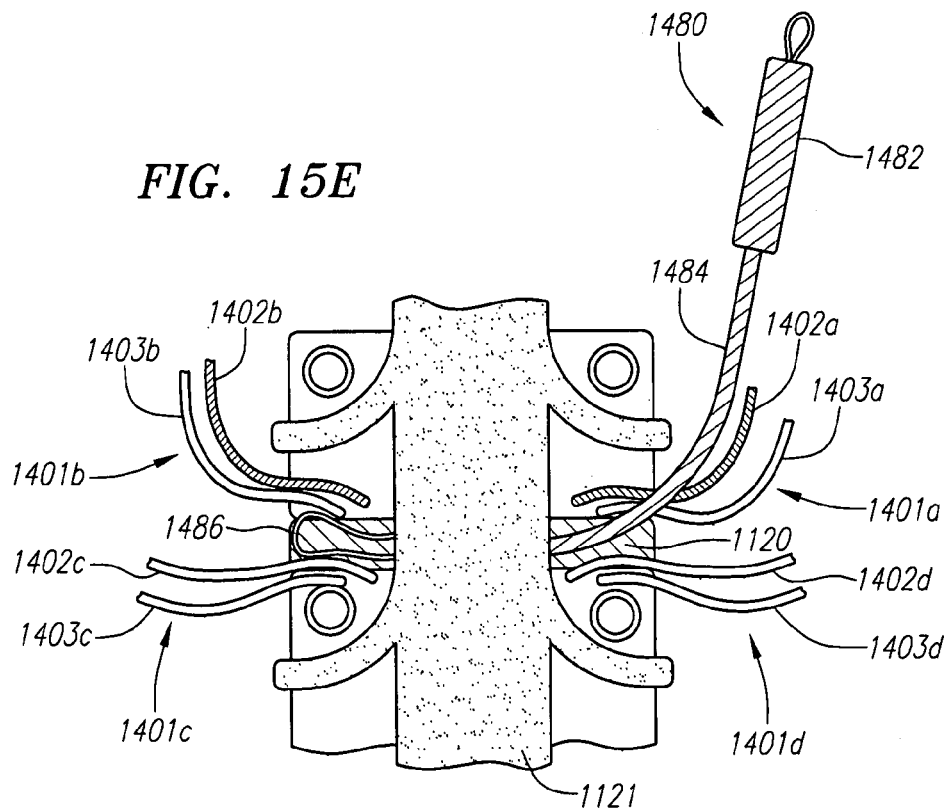
FIG. 15E is a posterior view of a coronal cross section of the spine, the embodiment of the invention drawn in FIG. 15B and the suture passing tool.

FIG. 15E is a posterior view of a coronal cross section of the spine, the embodiment of the invention drawn in FIG. 15B and the suture passing tool 1480. The distal loop 1486 of the suture passing tool 1480 was passed between the disc 1120 and the thecal sac 1121.

Figure 15F:
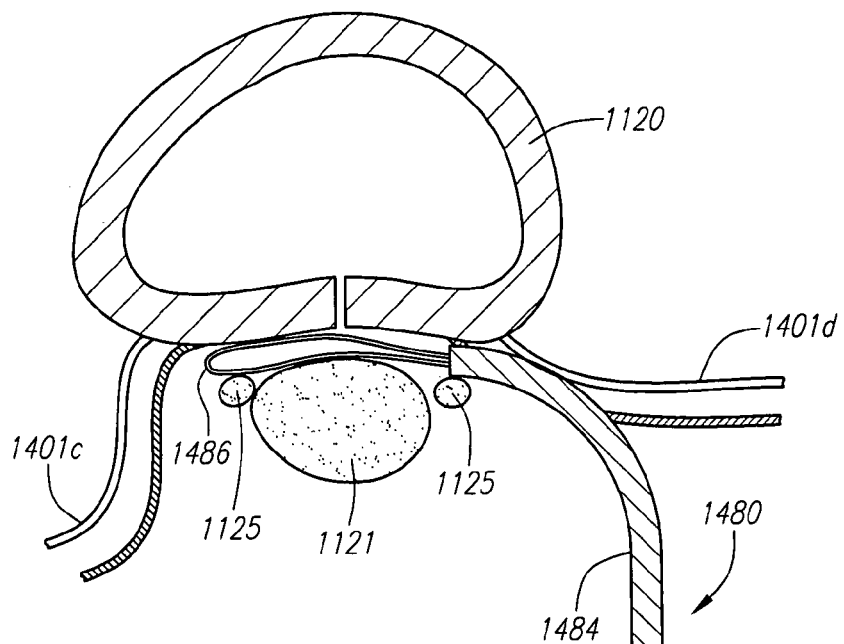
FIG. 15F is an axial cross section of the disc, the embodiment of the invention drawn in FIG. 15E and the suture passing tool passed between the disc and the thecal sac.

FIG. 15F is an axial cross section of the disc, the embodiment of the invention drawn in FIG. 15E and the suture passing tool 1480. The distal loop 1486 of the suture passing tool 1480 was passed between the disc 1120 and the thecal sac 1121. Fixation sutures 1401*c,d* have already been anchored into the vertebra caudal to the disc 1120.

Figure 15G:
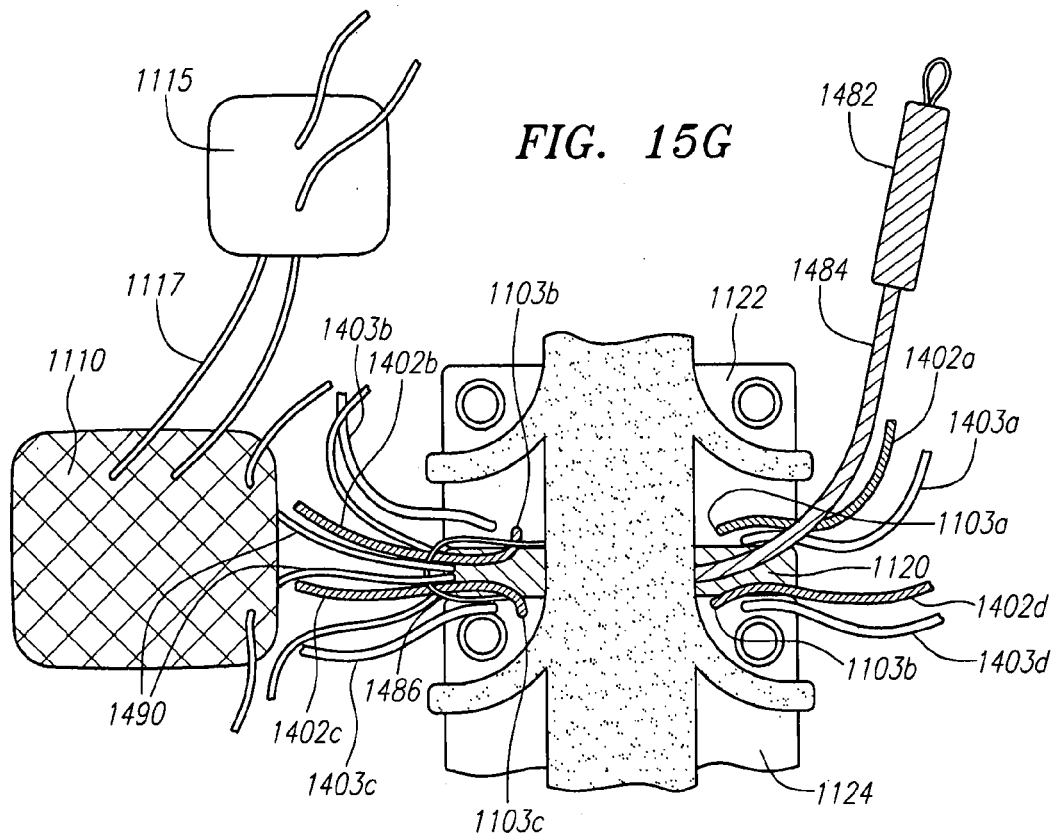
FIG. 15G is a posterior view of a coronal cross section of the spine, the embodiment of the invention drawn in FIGS. 5A and 5C, and the suture passing tool 1480.

FIG. 15G is a posterior view of a coronal cross section of the spine, the embodiment of the invention drawn in FIGS. 5A and 5C, and the suture passing tool 1480. The medial ends of the fixation sutures 1402*b,c* from the left side of the vertebrae were passed through the distal loop 1486 of the suture passer 1480. Sutures from the right side of the mesh were also passed through the distal loop of the suture passer. A positioning suture 1490 was also passed through the loop 1486 before both ends were threaded into the mesh patch 1110 so that the suture passing tool 1480 can be used to position the mesh patch 1110. The positioning suture 1490 is used to pull the mesh under the thecal sac. The positioning suture 1490 is removed after passing the mesh under the thecal sac.

Figure 15H:
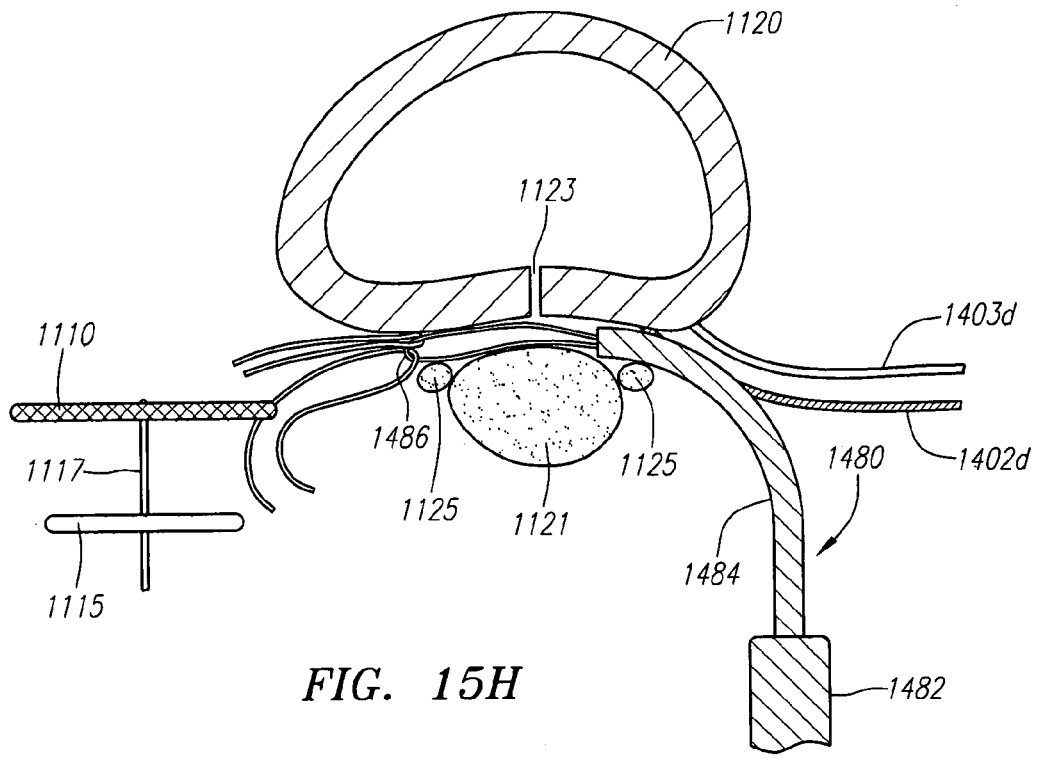
FIG. 15H is an axial cross section of a disc and the embodiment of the invention drawn in FIG. 15G.

FIG. 15H is an axial cross section of a disc and the embodiment of the invention drawn in FIG. 15G.

Figure 15I:
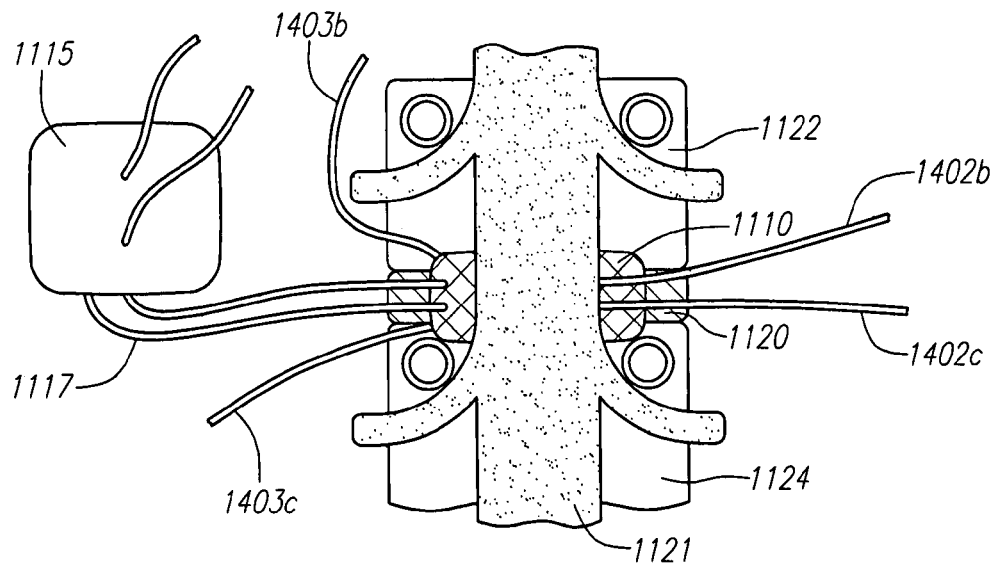
FIG. 15I is a posterior view of a coronal cross section of the spine and the embodiment of the invention drawn in FIG. 15G.

FIG. 15I is a posterior view of a coronal cross section of the spine and the embodiment of the invention drawn in FIG. 15G. The suture passing tool (not shown) was used to pull the medial ends 1402b,c of the fixation sutures from the left side of the vertebrae, under the thecal sac 1121 and out the right side of the spinal canal. The tool was also used to pull the mesh patch 1110 under the thecal sac 1121 and across the posterior aspect of the disc 1120. The cover component 1115 can be seen on the left side of the picture. The fixation sutures on the right side of the spinal canal were not drawn. The suture passing tool and the positioning sutures from the mesh patch were removed after passing the patch and the fixation sutures.

Figure 15J:
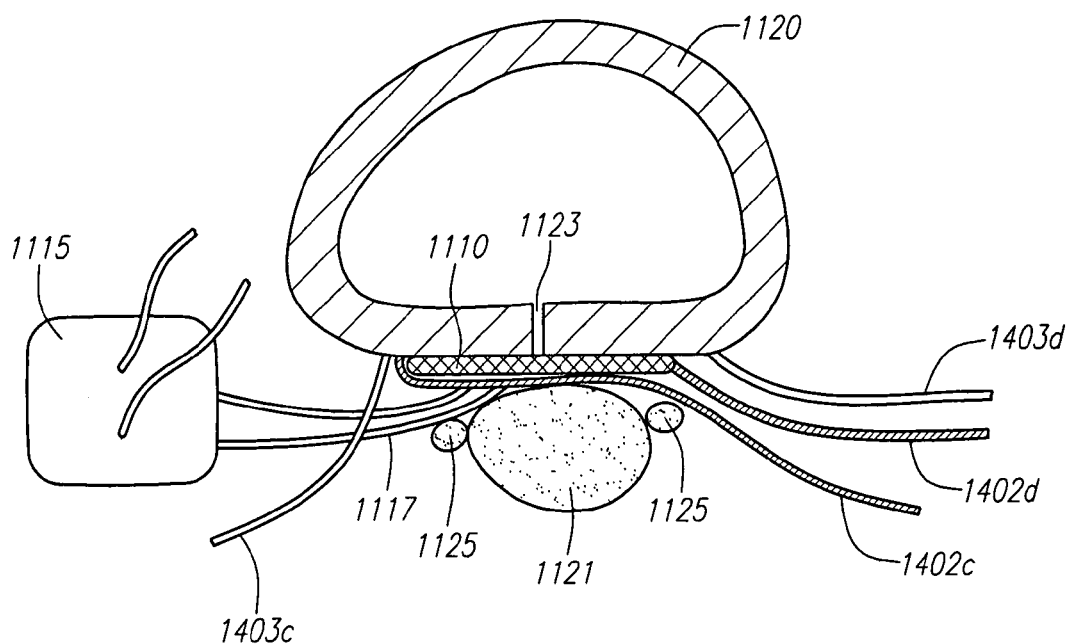
FIG. 15J is an axial cross section of a disc and the embodiment of the invention drawn in FIG. 15I.

FIG. 15J is an axial cross section of a disc and the embodiment of the invention drawn in FIG. 15I. The connecting suture 1117 passes through the left sides of the mesh patch 1110 and cover component 1115.

Figure 15K:
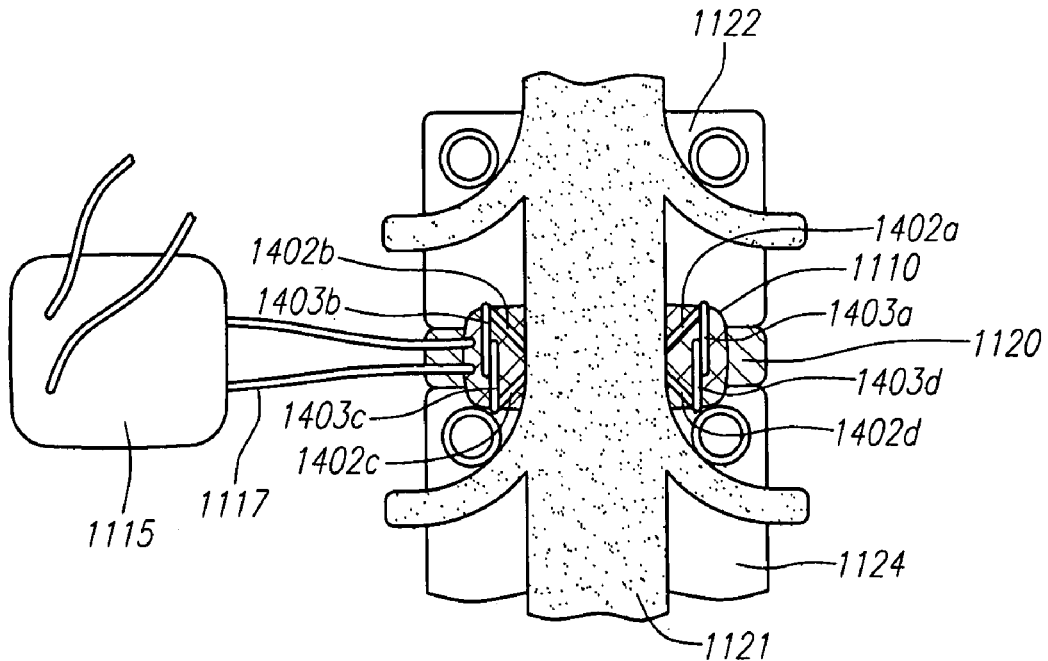
FIG. 15K is a posterior view of a coronal cross section of the spine and the embodiment of the invention drawn in FIG. 15I with the diagonal arms of the fixation sutures welded together from the right side of the spinal canal.

FIG. 15K is a posterior view of a coronal cross section of the spine and the embodiment of the invention drawn in FIG. 15I. The diagonal arms of the fixation sutures 1402a-d were welded together from the right side of the spinal canal. Tension was applied to the free ends of the welded fixation sutures to position the welded areas of the sutures over the central portion of the mesh patch 1110. The lateral arms of the left fixation sutures 1403b,c were welded from the left side of the spinal canal. The lateral arms of the right fixation sutures 1403a,d were welded from the right side of the spinal canal.

Figure 15L:
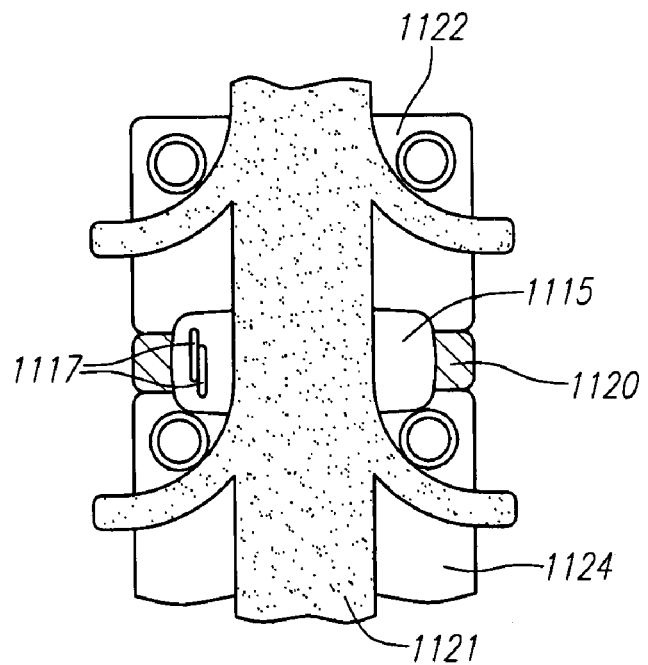
FIG. 15L is a posterior view of a coronal cross section of the spine and the embodiment of the invention drawn in FIG. 15K with an anti-adhesion cover.

FIG. 15L is a posterior view of a coronal cross section of the spine and the embodiment of the invention drawn in FIG. 15K. The anti-adhesion cover 1115 was passed between the thecal sac 1121 and the mesh patch 1110. The cover 1115 could be passed with the suture passing tool. The connecting suture 1117 was welded from the left side of the spinal canal.

FIG. 16A is a posterior view of an alternative embodiment of the invention drawn in FIG. 5C. A reinforcement band 1492 courses through or over the mesh patch 1110. The reinforcement band 1492 is preferably made of polyester or polypropylene. Alternatively, the band 1492 may be made of nylon, titanium, or other synthetic or natural material. The band 1492 has a higher tensile strength than the mesh. The band 1492 is preferably a closed loop. The loop can be square, circular or other shape. In one embodiment, the reinforcement band 1492 could be welded to the mesh component 1110. Alternative methods or devices may be used to fasten the devices such as adhesives, sutures, or staples. Applying the reinforcement member 1492 to the posterior surface of the mesh 1110 maximizes the area of the mesh that is available for connective tissue in-growth from the spinal tissues anterior to the mesh.

FIG. 16B is a posterior view of the embodiments of the invention drawn in FIG. 5J and 16A. The fixation sutures 1401a-d pass through the mesh 1110 and through the central portion of the high tensile strength loop 1492. Alternative fixation members may be fastened to the mesh central to the loop. The fixation members 1401a-d may pull on the reinforcement member 1492. The configuration permits the fixation members 401a-d to apply tension to the mesh without pulling through the mesh.

FIG. 17A is a posterior view of an alternative embodiment of the invention drawn in FIG. 16A. Reinforcing members or bands 1494 course through the mesh. The ends of the reinforcing bands 1494 have features that facilitate fastening of fixation members. For example, the ends of the bands may have reinforced circular openings 1495.

FIG. 17B is a posterior view of the embodiment of the invention drawn in FIG. 17A and FIG. 17 of provisional application entitled "Fastening Assemblies for disc Herniation repair and Methods of Use" (U.S. Application Ser. No. 60/808,795), which is hereby expressly incorporated by reference in its entirety. Sutures 1497 with enlarged ends 1498 of the fixation members were placed through the openings 1495 in the reinforced regions of the mesh 1110.

FIG. 18A is a posterior view of an alternative embodiment of the invention. The reinforcement component is a closed loop. The reinforcement component also has vertical 1496v, horizontal 1496h, and diagonal 1496d members. Portions of the reinforcement members are posterior to the mesh. For example, strands of reinforcement material may extend from the corners of the reinforcement square.

FIG. 18B is a posterior view of the embodiment of the invention drawn in FIG. 18A wherein fixation members 1402a-d have been welded or otherwise attached to the strands 1496 of the reinforcement component.

FIG. 19 is a posterior view of an alternative embodiment of the invention. The periphery of the mesh 1110 is reinforced with reinforcement members 1502. Diagonal reinforcement members 1504 also course across the mesh 1110.

FIG. 20 is a posterior view of an alternative embodiment of the invention drawn in FIG. 17A. The reinforcement members have openings 1495, vertical 1499v, horizontal 1499h, and diagonal components 1494.

FIG. 21A is a lateral view of an alternative embodiment of the invention drawn in FIG. 5D. The device 1510 is smaller than the device 1410 drawn in FIG. 5D. The device 1510 has two slots 1515 to receive sutures. Alternatively, the device 1510 could have one to three or more slots 1515.

FIG. 21B is a view of the top of the embodiment of the invention drawn in FIG. 21A, which illustrates base 1512 and posterior aspect 1514 attached generally perpendicularly to base 1512.

FIG. 22A is a posterior view of an alternative embodiment of the invention drawn in FIG. 9A. The device 1460 has features, such as slots 1462 that make the device more flexible in one direction (four small rectangles near the center of the device). The features help prevent the component compressing nerves should the component become separated from one or more fixation suture.

FIG. 22B is a lateral view of a portion of the embodiment of the invention drawn in FIG. 22A. The extension 1462 includes a slot feature 1463.

Figure 22C:
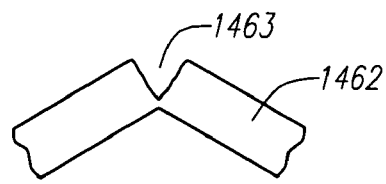
FIG. 22C is a lateral view of the embodiment of the invention drawn in FIG. 22B.

FIG. 22C is a lateral view of the embodiment of the invention drawn in FIG. 22B. The drawing illustrates how the extension 1462 bends easily in the direction opposite of the slot-like feature 1463.

Figure 22D:
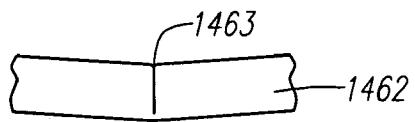
FIG. 22D is a lateral view of the embodiment of the invention drawn in FIG. 22C.

FIG. 22D is a lateral view of the embodiment of the invention drawn in FIG. 22C. The drawing illustrates how the extension 1462 resists bending in the direction of the slot-like feature 1463.

Figure 22E:
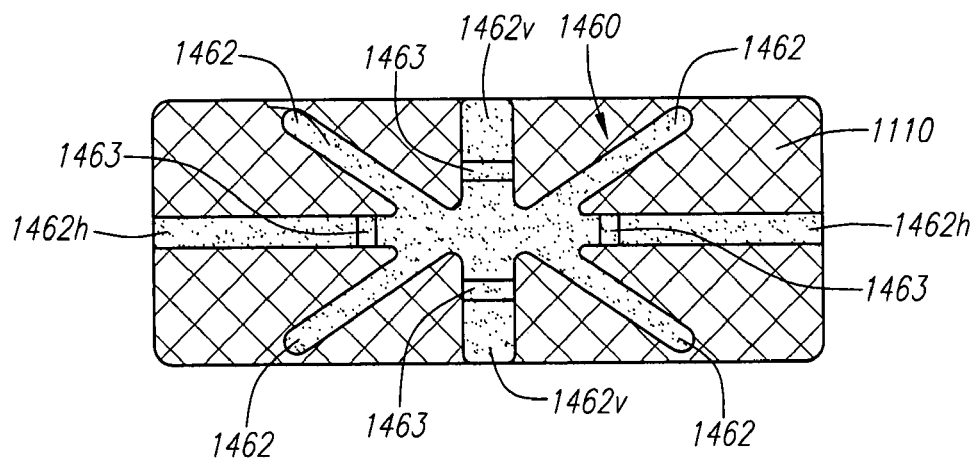
FIG. 22E is posterior view of the embodiment of the invention drawn in FIG. 22A and a mesh component.

FIG. 22E is posterior view of the embodiment of the invention drawn in FIG. 22A and a mesh component 1110. The selectively flexible component 1460 is attached to the mesh component 1110. The components are preferably attached along the vertical 1462v and horizontal 1462h members of the selectively flexible component 1460. The diagonal members 1462 are not attached to the mesh component 1110. The configuration enables fixation sutures to be welded to the device. The components can be attached with ultrasonic welds, adhesive, deformable features, or other mechanisms.

Figure 23A:
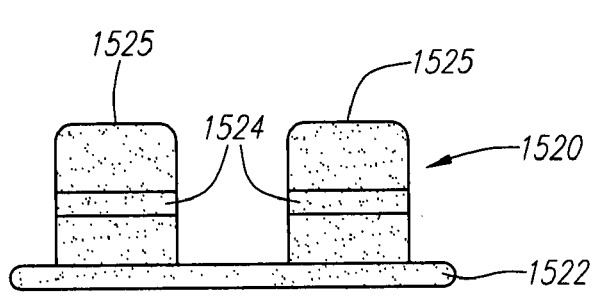
FIG. 23A is a lateral view of an alternative suture holding device having a base with posts having slots.

FIG. 23A is a lateral view of an alternative embodiment of the invention drawn in FIG. 21A. The suture-holding device 1520 has a base 1522 with posts 1525 having slots 1524. The posts 1525 are oriented generally perpendicular to the base 1522. The slots 1524 are used to hold the ends of sutures. The base 1522 of the device is preferably covered with an adhesive component.

Figure 23B:
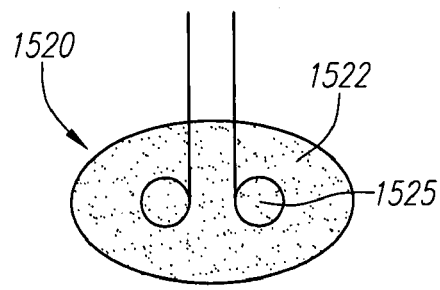
FIG. 23B is view of the top of the embodiment of the invention drawn in FIG. 23A and portions of two sutures.

FIG. 23B is view of the top of the embodiment of the invention drawn in FIG. 23A and portions of two sutures. The sutures are held in the slots 1524 of the device 1520. The sutures or the device adjacent to the slots 1524 are preferably reversibly deformable to facilitate the press-fit of the sutures into the device. The invention is designed to temporarily hold the sutures without injuring the sutures. The device 1520 is preferably made of a radiolucent polymer such as an elastomer.

Although the foregoing invention has, for the purposes of clarity and understanding, been described in some detail by way of illustration and example, it will be obvious that certain changes and modifications may be practiced which will still fall within the scope of the appended claims.

I claim:

1. A method for treating a defect in a vertebral disc having an annulus fibrosus containing nucleus pulposus, wherein the defect is in the annulus fibrosus, the method comprising the steps of:
   providing a device comprising a tubular body having a wall, pores located in the wall, first and second openings, and a lumen extending between the first and second openings;
   inserting the device into the defect in the annulus fibrosus so that nucleus pulposus tissue intentionally migrates from the vertebral disc through at least one of the first opening, the second opening, and the pores into the lumen of the tubular body and out of the other of the first or second opening; and
   wherein the device further comprises a first porous barrier located at one of the first or second openings.

2. A method for treating a defect in a vertebral disc having an annulus fibrosus containing nucleus pulposus, wherein the defect is in the annulus fibrosus, the method comprising the steps of:
   providing a device comprising a tubular body having a wall, pores located in the wall, first and second openings, and a lumen extending between the first and second openings;
   inserting the device into the defect in the annulus fibrosus so that nucleus pulposus tissue intentionally migrates from the vertebral disc through at least one of the first opening, the second opening, and the pores into the lumen of the tubular body and out of the other of the first or second opening; and
   wherein the tubular body does not fill the defect such that nucleus pulposus flows into and out of the vertebral disc through space between the tubular body and the annulus fibrosus.

3. A method for treating a defect in a vertebral disc having an annulus fibrosus containing nucleus pulposus, wherein the defect is in the annulus fibrosus, the method comprising the steps of:
   providing a device comprising a tubular body having a wall, pores located in the wall, first and second openings, and a lumen extending between the first and second openings; and
   inserting the device into the defect in the annulus fibrosus so that nucleus pulposus tissue intentionally migrates from the vertebral disc through at least one of the first opening, the second opening, and the pores into the lumen of the tubular body and out of the other of the first or second opening; and
   wherein the tubular body has external threads.

4. A method for treating a defect in a vertebral disc having an annulus fibrosus containing nucleus pulposus, wherein the defect is in the annulus fibrosus, the method comprising the steps of:
   providing a device comprising a tubular body having a wall, pores located in the wall, first and second openings, and a lumen extending between the first and second openings;
   inserting the device into the defect in the annulus fibrosus so that nucleus pulposus tissue intentionally migrates from the vertebral disc through at least one of the first opening, the second opening, and the pores into the lumen of the tubular body and out of the other of the first or second opening; and wherein:
   the defect in the annulus fibrosus has a sidewall; and
   the wall of the tubular body is positioned against the wall of the defect such that one of the openings is oriented into the vertebral disc and the other opening is oriented outwardly from the vertebral disc.

* * * * *